(12) United States Patent
Nickel

(10) Patent No.: US 10,654,900 B2
(45) Date of Patent: *May 19, 2020

(54) METHOD FOR TREATING PROSTATITIS UTILIZING THE PORE-FORMING PROTEIN PROAEROLYSIN PRX302

(71) Applicant: Sophiris Bio, Corp., La Jolla, CA (US)

(72) Inventor: J. Curtis Nickel, Kingston, CA (US)

(73) Assignee: Sophiris Bio, Corp., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/282,111

(22) Filed: Sep. 30, 2016

(65) Prior Publication Data

US 2017/0081370 A1    Mar. 23, 2017

Related U.S. Application Data

(63) Continuation of application No. 14/537,429, filed on Nov. 10, 2014, now abandoned, which is a continuation of application No. 13/608,995, filed on Sep. 10, 2012, now Pat. No. 8,901,070, which is a continuation of application No. 13/139,928, filed as application No. PCT/CA2009/001837 on Dec. 15, 2009, now Pat. No. 8,278,279.

(60) Provisional application No. 61/122,709, filed on Dec. 15, 2008.

(51) Int. Cl.
| | | |
|---|---|---|
| *A61K 47/60* | (2017.01) | |
| *A61K 47/64* | (2017.01) | |
| *A61K 47/68* | (2017.01) | |
| *A61K 38/16* | (2006.01) | |
| *A61K 45/06* | (2006.01) | |
| *A61K 38/00* | (2006.01) | |
| *C07K 14/195* | (2006.01) | |
| *C07K 16/28* | (2006.01) | |

(52) U.S. Cl.
CPC .......... *C07K 14/195* (2013.01); *A61K 38/164* (2013.01); *A61K 45/06* (2013.01); *A61K 47/60* (2017.08); *A61K 47/6425* (2017.08); *A61K 47/6869* (2017.08); *C07K 16/28* (2013.01); *A61K 38/00* (2013.01); *C07K 2319/30* (2013.01); *C07K 2319/33* (2013.01)

(58) Field of Classification Search
CPC .. C07K 14/195; C07K 16/28; C07K 2319/30; C07K 2319/33; A61K 45/06; A61K 38/00; A61K 38/164
See application file for complete search history.

(56) References Cited

U.S. PATENT DOCUMENTS

| | | |
|---|---|---|
| 6,403,640 B1 | 6/2002 | Stoner |
| 7,282,476 B2 | 10/2007 | Denmeade |
| 7,745,395 B2 | 6/2010 | Denmeade |
| 7,838,266 B2 | 11/2010 | Denmeade |
| 8,278,279 B2 | 10/2012 | Nickel |
| 8,901,070 B2 | 12/2014 | Nickel |
| 2002/0001588 A1 | 1/2002 | Sinha |
| 2010/0233191 A1 | 9/2010 | Buckley |
| 2011/0263480 A1 | 10/2011 | Nickel |
| 2013/0129751 A1 | 5/2013 | Nickel |
| 2015/0283203 A1 | 10/2015 | Nickel |

FOREIGN PATENT DOCUMENTS

| | | |
|---|---|---|
| JP | 2005520490 A | 7/2005 |
| JP | 2006104221 A | 4/2006 |
| JP | 2007126477 A | 5/2007 |
| WO | 2003018611 A2 | 3/2003 |
| WO | 2006133553 A1 | 12/2006 |
| WO | 2007056867 A1 | 5/2007 |
| WO | 2007140618 A1 | 12/2007 |
| WO | 2010069060 | 6/2010 |

OTHER PUBLICATIONS

Fitzhugh M. Bioworld. http://www.bioworld.com/content/sophiris-bph-drug-hits-primary-endpoint-phase-iii. Retrieved from the internet Feb. 13, 2018.*
Peabody J. (Apr. 5, 2015) Seeking Alpha. https://seekingalpha.com/article/3058166-sophiris-bio-maybe-not-a-left-for-dead-biotech. Retrieved from the internet Feb. 13, 2018.*
Hickman Hd, et al. (Dec. 2012). Human Immunology. 61(12):1339-1346. (https://doi.org/10.1016/S0198-8859(00)00216-0).*
Tahmatzopoulos A, et al. (Jun. 2004). Expert Opinion Pharmacother. 5(6):1279-1285. (DOI: 10.1517/14656566.5.6.1279).*
Williams et al., 'A prostate-specific antigen-activated channel-forming toxin as therapy for prostatic disease,' J Natl Cancer Inst vol. 99, 2007, pp. 376-385, XP008140709.
Kuo H.: 'Prostate botulinum A toxin injection—an alternative treatment for benign prostatic obstruction in poor surgical candidates' J. Urology vol. 65, 2004, pp. 670-674, XP004843223.
Sindhwani, P., et al, "Prostatitis and serum prostate-specific antigen," Curr Urol. Rep. Jul. 2005; 6(4):307-12.
Annonymous, "Surgery for Chronic Prostatitis", Prostate.net at https://prostate.net/articles/surgery-for-chronic-prostatitis, 4 pages, (2011).
Internation Application No. PCT/CA2009/001837; International Preliminary Report on Patentability, dated Jun. 21, 2011; 8 pages.
Internation Application No. PCT/CA2009/001837; International Search Report and Written Opinion of the International Search Authority, dated Feb. 24, 2010; 13 pages.
Krongrad, A. et al., "Laparoscopic Prostatectomy for Severely Symptomatic, Treatment-Refractory Chronic Prostatitis: Preliminary Observations from an Ongoing Phase II Clinical Trial", Urotoday Int. J. webpage at https://www.urotoday.com/volume-4-2011/vol-4-issue-2/48861-laparosco%E2%80%A6from-an-ongoing-phase-ii-clinical-trial.html?tmpl=component&print=1, 4(2): art 30, (2011).
U.S. Appl. No. 13/139,928; Non-Final Office Action dated Nov. 10, 2011; 9 pages.

(Continued)

Primary Examiner — Robert S Landsman
(74) Attorney, Agent, or Firm — Dennis A. Bennett; Stephanie M. Greer; Chris Marion

(57) ABSTRACT

The present disclosure includes methods and compositions for treating any condition involving prostatitis and similar diseases and/or conditions. These methods and compositions involve the use of targeted modified pore-forming proteins, including variant proaerolysin proteins.

9 Claims, No Drawings

Specification includes a Sequence Listing.

(56) References Cited

OTHER PUBLICATIONS

U.S. Appl. No. 13/139,928; Notice of Allowance dated May 29, 2012; 7 pages.
U.S. Appl. No. 14/537,429; Examiner Initiated Interview Summary dated Dec. 1, 2016; 1 page.
U.S. Appl. No. 14/537,429; Final Office Action dated Mar. 31, 2016; 5 pages.
U.S. Appl. No. 14/537,429; Non-Final Office Action dated Sep. 21, 2015; 9 pages.

* cited by examiner

SEQUENCE LISTING

```
<160> NUMBER OF SEQ ID NOS: 4

<210> SEQ ID NO 1
<211> LENGTH: 1410
<212> TYPE: DNA
<213> ORGANISM: Aeromonas hydrophilia
<220> FEATURE:
<221> NAME/KEY: CDS
<222> LOCATION: (1)..(1410)

<400> SEQUENCE: 1 gca gag ccc gtc tat cca gac cag ctt cgc ttg ttt tca ttg ggc caa      48
Ala Glu Pro Val Tyr Pro Asp Gln Leu Arg Leu Phe Ser Leu Gly Gln
1               5                   10                  15 ggg gtc tgt ggc gac aag tat cgc ccc gtc aat cga gaa gaa gcc caa      96
Gly Val Cys Gly Asp Lys Tyr Arg Pro Val Asn Arg Glu Glu Ala Gln
            20                  25                  30 agc gtt aaa agc aat att gtc ggc atg atg ggg caa tgg caa ata agc     144
Ser Val Lys Ser Asn Ile Val Gly Met Met Gly Gln Trp Gln Ile Ser
        35                  40                  45 ggg ctg gcc aac ggc tgg gtc att atg ggg ccg ggt tat aac ggt gaa     192
Gly Leu Ala Asn Gly Trp Val Ile Met Gly Pro Gly Tyr Asn Gly Glu
    50                  55                  60 ata aaa cca ggg aca gcg tcc aat acc tgg tgt tat ccg acc aat cct     240
Ile Lys Pro Gly Thr Ala Ser Asn Thr Trp Cys Tyr Pro Thr Asn Pro
65                  70                  75                  80 gtt acc ggt gaa ata ccg aca ctg tct gcc ctg gat att cca gat ggt     288
```

```
                Val Thr Gly Glu Ile Pro Thr Leu Ser Ala Leu Asp Ile Pro Asp Gly
                             85                  90                  95 gac gaa gtc gat gtg cag tgg cga ctg gta cat gac agt gcg aat ttc         336
Asp Glu Val Asp Val Gln Trp Arg Leu Val His Asp Ser Ala Asn Phe
            100                 105                 110 atc aaa cca acc agc tat ctg gcc cat tac ctc ggt tat gcc tgg gtg         384
Ile Lys Pro Thr Ser Tyr Leu Ala His Tyr Leu Gly Tyr Ala Trp Val
            115                 120                 125 ggc ggc aat cac agc caa tat gtc ggc gaa gac atg gat gtg acc cgt         432
Gly Gly Asn His Ser Gln Tyr Val Gly Glu Asp Met Asp Val Thr Arg
            130                 135                 140 gat ggc gac ggc tgg gtg atc cgt ggc aac aat gac ggc ggt tgt gac         480
Asp Gly Asp Gly Trp Val Ile Arg Gly Asn Asn Asp Gly Gly Cys Asp
145                 150                 155                 160 ggc tat cgc tgt ggt gac aag acg gcc atc aag gtc agc aac ttc gcc         528
Gly Tyr Arg Cys Gly Asp Lys Thr Ala Ile Lys Val Ser Asn Phe Ala
                165                 170                 175 tat aac ctg gat ccc gac agc ttc aag cat ggc gat gtc acc cag tcc         576
Tyr Asn Leu Asp Pro Asp Ser Phe Lys His Gly Asp Val Thr Gln Ser
            180                 185                 190 gac cgc cag ctg gtc aag act gtg gtg ggc tgg gcg gtc aac gac agc         624
Asp Arg Gln Leu Val Lys Thr Val Val Gly Trp Ala Val Asn Asp Ser
            195                 200                 205 gac acc ccc caa tcc ggc tat gac gtc acc ctg cgc tac gac aca gcc         672
Asp Thr Pro Gln Ser Gly Tyr Asp Val Thr Leu Arg Tyr Asp Thr Ala
210                 215                 220 acc aac tgg tcc aag acc aac acc tat ggc ctg agc gag aag gtg acc         720
Thr Asn Trp Ser Lys Thr Asn Thr Tyr Gly Leu Ser Glu Lys Val Thr
225                 230                 235                 240 acc aag aac aag ttc aag tgg cca ctg gtg ggg gaa acc caa ctc tcc         768
Thr Lys Asn Lys Phe Lys Trp Pro Leu Val Gly Glu Thr Gln Leu Ser
                245                 250                 255 atc gag att gct gcc aat cag tcc tgg gcg tcc cag aac ggg ggc tcg         816
Ile Glu Ile Ala Ala Asn Gln Ser Trp Ala Ser Gln Asn Gly Gly Ser
            260                 265                 270 acc acc acc tcc ctg tct cag tcc gtg cga ccg act gtg ccg gcc cgc         864
Thr Thr Thr Ser Leu Ser Gln Ser Val Arg Pro Thr Val Pro Ala Arg
            275                 280                 285 tcc aag atc ccg gtg aag ata gag ctc tac aag gcc gac atc tcc tat         912
Ser Lys Ile Pro Val Lys Ile Glu Leu Tyr Lys Ala Asp Ile Ser Tyr
            290                 295                 300 ccc tat gag ttc aag gcc gat gtc agc tat gac ctg acc ctg agc ggc         960
Pro Tyr Glu Phe Lys Ala Asp Val Ser Tyr Asp Leu Thr Leu Ser Gly
305                 310                 315                 320 ttc ctg cgc tgg ggc ggc aac gcc tgg tat acc cac ccg gac aac cgt        1008
Phe Leu Arg Trp Gly Gly Asn Ala Trp Tyr Thr His Pro Asp Asn Arg
                325                 330                 335 ccg aac tgg aac cac acc ttc gtc ata ggt ccg tac aag gac aag gcg        1056
Pro Asn Trp Asn His Thr Phe Val Ile Gly Pro Tyr Lys Asp Lys Ala
            340                 345                 350 agc agc att cgg tac cag tgg gac aag cgt tac atc ccg ggt gaa gtg        1104
Ser Ser Ile Arg Tyr Gln Trp Asp Lys Arg Tyr Ile Pro Gly Glu Val
            355                 360                 365 aag tgg tgg gac tgg aac tgg acc ata cag cag aac ggt ctg tct acc        1152
Lys Trp Trp Asp Trp Asn Trp Thr Ile Gln Gln Asn Gly Leu Ser Thr
            370                 375                 380 atg cag aac aac ctg gcc aga gtg ctg cgc ccg gtg cgg gcg ggg atc        1200
Met Gln Asn Asn Leu Ala Arg Val Leu Arg Pro Val Arg Ala Gly Ile
385                 390                 395                 400
```

```
acc ggt gat ttc agt gcc gag agc cag ttt gcc ggc aac ata gag atc    1248
Thr Gly Asp Phe Ser Ala Glu Ser Gln Phe Ala Gly Asn Ile Glu Ile
            405                 410                 415 ggt gct ccc gtg ccg ctc gcg gct gac agc aag gtg cgt cgt gct cgc    1296
Gly Ala Pro Val Pro Leu Ala Ala Asp Ser Lys Val Arg Arg Ala Arg
420                 425                 430 agt gtg gac ggc gct ggt caa ggc ctg agg ctg gag atc ccg ctc gat    1344
Ser Val Asp Gly Ala Gly Gln Gly Leu Arg Leu Glu Ile Pro Leu Asp
        435                 440                 445 gcg caa gag ctc tcc ggg ctt ggc ttc aac aac gtc agc ctc agc gtg    1392
Ala Gln Glu Leu Ser Gly Leu Gly Phe Asn Asn Val Ser Leu Ser Val
    450                 455                 460 acc cct gct gcc aat caa                                            1410
Thr Pro Ala Ala Asn Gln
465                 470

<210> SEQ ID NO 2
<211> LENGTH: 470
<212> TYPE: PRT
<213> ORGANISM: Aeromonas hydrophilia

<400> SEQUENCE: 2

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270
```

```
Thr Thr Thr Ser Leu Ser Gln Ser Val Arg Pro Thr Val Pro Ala Arg
            275                 280                 285

Ser Lys Ile Pro Val Lys Ile Glu Leu Tyr Lys Ala Asp Ile Ser Tyr
        290                 295                 300

Pro Tyr Glu Phe Lys Ala Asp Val Ser Tyr Asp Leu Thr Leu Ser Gly
305                 310                 315                 320

Phe Leu Arg Trp Gly Asn Ala Trp Tyr Thr His Pro Asp Asn Arg
                325                 330                 335

Pro Asn Trp Asn His Thr Phe Val Ile Gly Pro Tyr Lys Asp Lys Ala
                340                 345                 350

Ser Ser Ile Arg Tyr Gln Trp Asp Lys Arg Tyr Ile Pro Gly Glu Val
            355                 360                 365

Lys Trp Trp Asp Trp Asn Trp Thr Ile Gln Gln Asn Gly Leu Ser Thr
        370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser Lys Val Arg Arg Ala Arg
                420                 425                 430

Ser Val Asp Gly Ala Gly Gln Gly Leu Arg Leu Glu Ile Pro Leu Asp
            435                 440                 445

Ala Gln Glu Leu Ser Gly Leu Gly Phe Asn Asn Val Ser Leu Ser Val
                450                 455                 460

Thr Pro Ala Ala Asn Gln
465                 470

<210> SEQ ID NO 3
<211> LENGTH: 1410
<212> TYPE: DNA
<213> ORGANISM: Artificial Sequence
<220> FEATURE:
<223> OTHER INFORMATION: Proaerolysin with a PSA sequence subst -continued

```
              100                 105                 110
atc aaa cca acc agc tat ctg gcc cat tac ctc ggt tat gcc tgg gtg      384
Ile Lys Pro Thr Ser Tyr Leu Ala His Tyr Leu Gly Tyr Ala Trp Val
        115                 120                 125 ggc ggc aat cac agc caa tat gtc ggc gaa gac atg gat gtg acc cgt      432
Gly Gly Asn His Ser Gln Tyr Val Gly Glu Asp Met Asp Val Thr Arg
130                 135                 140 gat ggc gac ggc tgg gtg atc cgt ggc aac aat gac ggc ggt tgt gac      480
Asp Gly Asp Gly Trp Val Ile Arg Gly Asn Asn Asp Gly Gly Cys Asp
145                 150                 155                 160 ggc tat cgc tgt ggt gac aag acg gcc atc aag gtc agc aac ttc gcc      528
Gly Tyr Arg Cys Gly Asp Lys Thr Ala Ile Lys Val Ser Asn Phe Ala
                165                 170                 175 tat aac ctg gat ccc gac agc ttc aag cat ggc gat gtc acc cag tcc      576
Tyr Asn Leu Asp Pro Asp Ser Phe Lys His Gly Asp Val Thr Gln Ser
        180                 185                 190 gac cgc cag ctg gtc aag act gtg gtg ggc tgg gcg tcc aac gac agc      624
Asp Arg Gln Leu Val Lys Thr Val Val Gly Trp Ala Val Asn Asp Ser
        195                 200                 205 gac acc ccc caa tcc ggc tat gac gtc acc ctg cgc tac gac aca gcc      672
Asp Thr Pro Gln Ser Gly Tyr Asp Val Thr Leu Arg Tyr Asp Thr Ala
210                 215                 220 acc aac tgg tcc aag acc aac acc tat ggc ctg agc gag aag gtg acc      720
Thr Asn Trp Ser Lys Thr Asn Thr Tyr Gly Leu Ser Glu Lys Val Thr
225                 230                 235                 240 acc aag aac aag ttc aag tgg cca ctg gtg ggg gaa acc caa ctc tcc      768
Thr Lys Asn Lys Phe Lys Trp Pro Leu Val Gly Glu Thr Gln Leu Ser
                245                 250                 255 atc gag att gct gcc aat cag tcc tgg gcg tcc cag aac ggg ggc tcg      816
Ile Glu Ile Ala Ala Asn Gln Ser Trp Ala Ser Gln Asn Gly Gly Ser
        260                 265                 270 acc acc acc tcc ctg tct cag tcc gtg cga ccg act gtg ccg gcc cgc      864
Thr Thr Thr Ser Leu Ser Gln Ser Val Arg Pro Thr Val Pro Ala Arg
        275                 280                 285 tcc aag atc ccg gtg aag ata gag ctc tac aag gcc gac atc tcc tat      912
Ser Lys Ile Pro Val Lys Ile Glu Leu Tyr Lys Ala Asp Ile Ser Tyr
        290                 295                 300 ccc tat gag ttc aag gcc gat gtc agc tat gac ctg acc ctg agc ggc      960
Pro Tyr Glu Phe Lys Ala Asp Val Ser Tyr Asp Leu Thr Leu Ser Gly
305                 310                 315                 320 ttc ctg cgc tgg ggc ggc aac gcc tgg tat acc cac ccg gac aac cgt     1008
Phe Leu Arg Trp Gly Gly Asn Ala Trp Tyr Thr His Pro Asp Asn Arg
                325                 330                 335 ccg aac tgg aac cac acc ttc gtc ata ggt ccg tac aag gac aag gcg     1056
Pro Asn Trp Asn His Thr Phe Val Ile Gly Pro Tyr Lys Asp Lys Ala
        340                 345                 350 agc agc att cgg tac cag tgg gac aag cgt tac atc ccg ggt gaa gtg     1104
Ser Ser Ile Arg Tyr Gln Trp Asp Lys Arg Tyr Ile Pro Gly Glu Val
        355                 360                 365 aag tgg tgg gac tgg aac tgg acc ata cag cag aac ggt ctg tct acc     1152
Lys Trp Trp Asp Trp Asn Trp Thr Ile Gln Gln Asn Gly Leu Ser Thr
        370                 375                 380 atg cag aac aac ctg gcc aga gtg ctg cgc ccg gtg cgg gcg ggg atc     1200
Met Gln Asn Asn Leu Ala Arg Val Leu Arg Pro Val Arg Ala Gly Ile
385                 390                 395                 400 acc ggt gat ttc agt gcc gag agc cag ttt gcc ggc aac ata gag atc     1248
Thr Gly Asp Phe Ser Ala Glu Ser Gln Phe Ala Gly Asn Ile Glu Ile
                405                 410                 415 ggt gct ccc gtg ccg ctc gcg gct gac agc cat tcc tcc aag ctg cag     1296
```

```
Gly Ala Pro Val Pro Leu Ala Ala Asp Ser His Ser Lys Leu Gln
                420                 425                 430 agt gtg gac ggc gct ggt caa ggc ctg agg ctg gag atc ccg ctc gat     1344
Ser Val Asp Gly Ala Gly Gln Gly Leu Arg Leu Glu Ile Pro Leu Asp
            435                 440                 445 gcg caa gag ctc tcc ggg ctt ggc ttc aac aac gtc agc ctc agc gtg     1392
Ala Gln Glu Leu Ser Gly Leu Gly Phe Asn Asn Val Ser Leu Ser Val
450                 455                 460 acc cct gct gcc aat caa                                             1410
Thr Pro Ala Ala Asn Gln
465                 470

<210> SEQ ID NO 4
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 4

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285
```

```
Ser Lys Ile Pro Val Lys Ile Glu Leu Tyr Lys Ala Asp Ile Ser Tyr
    290             295             300

Pro Tyr Glu Phe Lys Ala Asp Val Ser Tyr Asp Leu Thr Leu Ser Gly
305             310             315                         320

Phe Leu Arg Trp Gly Gly Asn Ala Trp Tyr Thr His Pro Asp Asn Arg
            325             330                 335

Pro Asn Trp Asn His Thr Phe Val Ile Gly Pro Tyr Lys Asp Lys Ala
                340             345             350

Ser Ser Ile Arg Tyr Gln Trp Asp Lys Arg Tyr Ile Pro Gly Glu Val
        355             360             365

Lys Trp Trp Asp Trp Asn Trp Thr Ile Gln Gln Asn Gly Leu Ser Thr
    370             375             380

Met Gln Asn Asn Leu Ala Arg Val Leu Arg Pro Val Arg Ala Gly Ile
385             390             395                         400

Thr Gly Asp Phe Ser Ala Glu Ser Gln Phe Ala Gly Asn Ile Glu Ile
            405             410             415

Gly Ala Pro Val Pro Leu Ala Ala Asp Ser His Ser Ser Lys Leu Gln
            420             425             430

Ser Val Asp Gly Ala Gly Gln Gly Leu Arg Leu Glu Ile Pro Leu Asp
        435             440             445

Ala Gln Glu Leu Ser Gly Leu Gly Phe Asn Asn Val Ser Leu Ser Val
    450             455             460

Thr Pro Ala Ala Asn Gln
465             470
```

METHOD FOR TREATING PROSTATITIS UTILIZING THE PORE-FORMING PROTEIN PROAEROLYSIN PRX302

CROSS REFERENCE TO RELATED APPLICATION

This application is a continuation application of U.S. patent application Ser. No. 14/537,429 filed on Nov. 10, 2014, now abandoned, which is continuation of U.S. patent application Ser. No. 13/608,995 filed on Sep. 10, 2012, now U.S. Pat. No. 8,901,070, which is a continuation of U.S. patent application Ser. No. 13/139,928 filed on Jul. 14, 2011, now U.S. Pat. No. 8,278,279, which is a U.S. national stage filing under 35 U.S.C. 371 of PCT/CA2009/001837 filed on Dec. 15, 2009, which claims the benefit of priority of U.S. Provisional Application No. 61/122,709 filed on Dec. 15, 2008, the contents of which are incorporated herein by reference in their entirety.

FIELD OF THE DISCLOSURE

This disclosure relates to the field of prostatitis, and in particular, to the use of modified pore-forming proteins for the treatment of prostatitis.

BACKGROUND

It is believed that chronic prostatitis is one of the most common reasons why men visit urologists, even being characterized as the condition responsible for more outpatient visits than benign prostatic hyperplasia ("BPH") or prostate cancer. At least one report states that 35-50% of men will be affected by prostatitis at some time in their life. The treatments conventionally used to treat this condition have been generally problematic; most of the treatments have provided little hope that the condition could be predictably treated in a manner which could successfully alleviate the pain experienced by a large percentage of these individuals. Indeed, prostatitis has been termed "a waste basket of clinical ignorance" because of the lack of knowledge about the basic epidemiology of the disease and also the diagnosis and treatments available for the same. See Collins et al., *J. Urology*, 159: 1224-1228, 1998.

Unlike BPH, which occurs primarily in older men, prostatitis can occur in both younger (men in age groups of 18-50) and older men (over the age of 50), with the median reported patient age at about 40 years of age. It is thought to be the most common urologic diagnosis for men less than 50 years of age.

There are several classifications or types of prostatitis, each of which may have different characteristics, manifestations, symptoms, or treatment protocols. Type I is acute bacterial prostatitis; Type II is chronic bacterial prostatitis; Type III is chronic (non-bacterial) prostatitis and/or chronic pelvic pain syndrome (CPPS); and Type IV is asymptomatic inflammatory prostatitis. See Nickel et al., *Urology*, 54(2): 229-233, 1999. Type III prostatitis (non-bacterial chronic prostatitis) is generally associated with urogenital pain in the absence of uropathogenic bacteria detected by standard microbiological methodology. Id. Type III prostatitis can be further defined as IIIA (inflammatory) or IIIB (noninflammatory). The IIIA inflammatory type prostatitis can be identified based on the presence of leukocytes in expressed prostatic secretions or fluids, post prostatic massage urine, or semen, while the IIIB non-inflammatory type can be identified based on the absence of detectable leukocytes in similar specimens. This type of prostatitis may also be associated with variable voiding, sexual dysfunction, and/or psychologic alterations (particularly depression).

Only a small number of reported prostatitis cases are believed to be of the Type I or acute bacterial type, while the remaining classes of chronic prostatitis may affect an estimated 30 million men in the United States. As such, chronic prostatitis is a major health care issue.

To assess the severity of prostatitis symptoms and responsiveness to certain therapies, certain standardized assessment protocols can be used. For example, the NIH Chronic Prostatitis Symptom Index (NIH-CPSI) was nominated as the standard of choice for clinical trials occurring after 1999. Similarly, other scores, indexes and surveys can be used to diagnose or assess treatment efficacy, such as an International Prostate Symptom Score (IPSS) system of seven questions.

Various treatment protocols have been used to attempt to treat prostatitis. While Type I and II may be managed successfully with specific antibiotics that penetrate the prostate, patients having Type III prostatitis have had lesser degrees of response success when treated with antibiotics. Other treatment regimes include other drugs such as alpha-blocker therapy (for obstructive voiding), and anti-inflammatory agents. In addition, or alternatively, the physician may suggest lifestyle changes such as diet (such as the reduction of the intake of caffeine), exercise, sexual activity, and/or supportive psychotherapy.

Additional treatment protocols suggested include repetitive prostate massage via the rectum as performed by the patient or assisted by another (such as 2-3 times per week), phytotherapy, transurethral microwave thermo (heat) therapy, or even radical transurethral resection of the prostate, radical open prostatectomy, and bladder neck surgery. Unfortunately, these prostatitis treatments result in a dismal cure rate and an unacceptably high relapse or recurrence rate.

In view of the above, there remains a need to provide improved and/or alternative treatments for chronic prostatitis.

SUMMARY OF THE DISCLOSURE

Disclosed herein are methods of using modified pore-forming proteins for treating prostatitis and similar diseases and/or conditions. In some embodiments, modified pore-forming proteins decrease prostate size (volume) in a subject, for example relative to a similarly situated subject not receiving the treatment.

The methods of the present disclosure involve the use one or more modified pore-forming proteins. These modified proteins are typically derived from a naturally-occurring pore-forming protein, such as pore-forming proteins comprising one or more prostate-selective modifications.

Some embodiments involve the use of a modified pore-forming protein in the preparation of a medicament for decreasing prostate size in a subject, and/or treating prostatitis or similar diseases or conditions.

Some embodiments include a method of decreasing prostate size in a subject, wherein the method includes administering to said subject a therapeutically effective amount of a composition comprising a modified pore-forming protein. In some embodiments of the disclosure, the methods include treating prostatitis and related diseases and conditions, such as chronic prostatitis.

Some embodiments include methods that use a modified proaerolysin protein for the treatment of prostate specific conditions and/or diseases, particularly prostatitis (such as chronic prostatitis). For example, an exemplary modified proaerolysin protein has an amino acid sequence set forth by SEQ ID NO: 4. In one example, the composition includes a modified proaerolysin protein with an amino acid sequence set forth by SEQ ID NO: 4 and a polyhistidine tag (e.g., a 6-Histidine C-terminal tag).

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NOS: 1 and 2 show the nucleic acid sequence and amino acid sequence, respectively, of wild-type proaerolysin.

SEQ ID NOS: 3 and 4 show the nucleic acid sequence and amino acid sequence, respectively, of a variant proaerolysin, in which the furin site of proaerolysin has been replaced with a PSA cleavage site (referred to herein as PRX302).

DETAILED DESCRIPTION OF THE DISCLOSURE

Disclosed herein are methods for treating prostatitis and similar diseases and/or conditions using modified pore-forming proteins. The methods are particularly useful in treating any prostate disease and/or condition that involve increased prostate size due to inflammation or infection of the prostate. In these embodiments use of the methods result in a decrease in inflammation and resulting neuropathy sufficient to produce a beneficial result for the patient, e.g., reduction or elimination of symptoms.

Some embodiments of the present disclosure include a method for treating prostatitis and/or similar diseases or conditions in a subject, including administering to said subject an effective amount of a modified pore-forming protein.

Some embodiments include the use of a modified pore-forming protein in the preparation of a medicament for the treatment of prostatitis and/or similar diseases or conditions.

In some examples, the methods use a modified proaerolysin protein for the treatment of certain prostate specific conditions and/or diseases, such as prostatitis including chronic prostatitis. A modified proaerolysin protein can include one or more mutations in a large lobe binding domain, and/or one or more prostate-specific modifications selected from a prostate-specific targeting domain capable of selectively targeting prostate cells and/or an activation sequence cleavable by a prostate-specific protease, wherein said modified proaerolysin is capable of selectively killing prostate cells.

The methods of the present disclosure involve one or more modified pore-forming proteins (MPPs). These modified proteins are typically derived from a naturally-occurring pore-forming protein (nPPs), typically including one or more prostate-selective modifications. These modifications may include one or more of a variety of mechanisms for providing a prostate specific cleavage site. In exemplary embodiments of the disclosure, these modifications are selected from an activation sequence cleavable by a prostate-specific protease, and/or one or more prostate-specific targeting domains capable of selectively targeting prostate cells. In one example, the modifications result in a modified pore-forming protein or construct that is capable of selectively targeting prostate cells, and subsequently treating the prostate cells to affect one or more functions.

In a particular embodiment, a composition includes an isolated MMP and an affinity tag that does not interfere with MMP function, such as a polyhistidine tag. In one example, the polyhistidine tag includes six sequential histidine residues and is attached to the C-terminus and/or N-terminus of the MMP. For example, the polyhistidine tag (e.g., a 6-His tag) can be attached to the C-terminus of an MMP that includes the amino acid sequence set forth by SEQ ID NO: 4.

As noted above, the MPPs are derived from naturally-occurring pore-forming proteins (nPPs). While not intending to be limited to a particular mode of action, it is believed that the MPPs kill cells by inserting into the membrane and forming pores or channels in the cell membranes of target cells, resulting in cell death. In one embodiment, the MPP inserts into the cell membrane irreversibly, and thus bystander cells are not affected. The MPPs can include prostate-selective modifications that result in the ability of the MPPs to selectively target prostate cells relative to cells from other tissues. The MPPs are capable of selectively killing prostate cells in vivo, and are capable of decreasing the weight or volume of prostate gland in vivo. Thus, the MPPs of the present disclosure may be used alone, or in combination with other therapies for the treatment of prostatitis, including, but not limited to alpha-blocker therapy (for obstructive voiding), antibiotics, anti-inflammatory agents, alterations in lifestyle such as diet (such as the reduction of the intake of caffeine), exercise, sexual activity, and/or supportive psychotherapy or "coping mechanisms". This is in contrast to the methods described in U.S. Patent Application No. 20040235095 which describes the use of modified cytolytic proteins to treat localized or metastatic prostate cancer.

TERMS

Unless defined otherwise, all technical and scientific terms used herein have the same meaning as commonly understood by one of ordinary skill in the art to which this disclosure belongs.

The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., and Lakowicz, J. R. Principles of Fluorescence Spectroscopy, New York: Plenum Press (1983) for fluorescence techniques). Standard techniques are used for chemical syntheses, chemical analyses, and biological assays. As employed throughout the disclosure, the following terms, unless otherwise indicated, shall be understood to have the following meanings.

As used herein, the term "about" refers to a +/−10% variation from the nominal value. It is to be understood that such a variation is always included in any given value provided herein, whether or not it is specifically referred to.

The term "ameliorate" includes the arrest, prevention, decrease, or improvement in one or more the symptoms, signs, and features of the disease or disorder being treated, both temporary and long-term.

The term "animal," as used herein refers to both human and non-human animals, including, but not limited to, mammals, birds and fish.

The phrase "in combination with one or more additional therapeutic agents or treatments" with regards to administration of the proteins of the disclosure, is intended to include simultaneous (concurrent) administration and consecutive administration. Consecutive administration is intended to encompass administration of the therapeutic agent(s) or additional treatment and the compound(s) of the disclosure to the subject in various orders and via various routes.

The term "prostate-specific" as used herein refers to a substance, or a component or part of the substance that is selective to prostate cells rather than other cell types. For example, a prostate specific entity/moiety can be selectively expressed by prostate cells, selectively associated with prostate cells, selectively activated by prostate cells, be capable of selectively binding to prostate cells, or the like.

The term "prostate-specific activation sequence," as used herein, refers to a sequence of amino acid residues that incorporates one or more prostate-specific protease cleavage sites. These sites are typically selectively cleaved or hydrolysed by a prostate-specific protease.

The term "prostate-specific targeting domain," as used herein, refers to a molecule, such as a peptide, ligand, toxin, or antibody that is capable of selectively binding to a prostate cell rather than to other cell types.

The term "selectively hybridize," as used herein, refers to the ability of a nucleic acid to bind specifically to a second nucleic acid. Polynucleotides, oligonucleotides, and fragments thereof selectively hybridize to target nucleic acid strands under hybridization and wash conditions that minimize appreciable amounts of detectable binding to non-specific nucleic acids. High stringency conditions can be used to achieve selective hybridization conditions as known in the art and discussed herein. Typically, hybridization and washing conditions are performed at high stringency according to conventional hybridization techniques.

The term "subject" or "patient" as used herein refers to an animal in need of treatment.

The terms "therapy" and "treatment" or "treating" refer to an intervention performed with the intention of improving a subject's status. It is intended that any beneficial result that is achieved is included within the scope of these terms. The improvement can be subjective or objective and is related to ameliorating the symptoms associated with, preventing the development of, or altering the pathology of a disease or disorder being treated. Thus, the terms "therapy" and "treatment" are used in the broadest sense (and as used interchangeably herein), refer to, and include the prevention, (prophylaxis), moderation, reduction, and/or curing of a disease or disorder at various stages. Preventing deterioration of a subject's status is also encompassed by the term. Subjects in need of therapy/treatment thus include those already having the disease or disorder as well as those prone to, or at risk of developing, the disease or disorder and those in whom the disease or disorder is to be prevented.

The term "therapeutically effective amount" is an amount of a composition sufficient to achieve a desired biological effect, for example an amount that is effective to reduce one or more signs or symptoms associated with any prostate disease and/or condition that involve increased prostate size due to inflammation or infection of the prostate. For example, a therapeutically effective amount is an amount of a composition that results in a decrease in inflammation and resulting neuropathy sufficient to produce a beneficial result for the patient, e.g., reduction or elimination of symptoms.

In one example, a therapeutically effective amount is an amount that reduces or inhibits one or more symptoms associated with non-bacterial chronic prostatitis (such as Type IIIA prostatitis), such as a reduction in the presence of leukocytes in expressed prostatic secretions or fluids, post prostatic massage urine, or semen (e.g., at least a 10%, 20%, 30%, 50%, 70%, 80%, 90%, or 95% reduction in detectable leukocytes, for example as compared to prior to the treatment, or as compared to a subject having non-bacterial chronic prostatitis but not receiving the therapy). In other examples, a therapeutically effective amount is an amount that reduces prostate size (e.g., volume), such as at least a 10%, 20%, 30%, 50%, 70%, 80%, 90%, or 95% reduction in size (for example as compared to prior to the treatment, or as compared to a subject having non-bacterial chronic prostatitis but not receiving the therapy), thereby reducing the one or more symptoms associated with the condition, such as variable voiding, sexual dysfunction, and/or psychologic alterations (particularly depression).

An effective amount of a MPP can be administered in a single dose, or in several doses, for example daily, during a course of treatment. However, the effective amount of will be dependent on the subject being treated, the severity and type of the condition being treated, and the manner of administration. For example, a therapeutically effective amount of a MPP can vary from about 1-10 mg per 70 kg body weight, for example about 2.8 mg, if administered iv and about 10-100 mg per 70 kg body weight, for example about 28 mg, if administered intraprostatically. In addition, a therapeutically effective amount of prostate cells lysed by the MPP to result in decreased inflammation can vary from about $10^6$ to $10^8$ cells.

The term "Type III prostatitis" as used herein refers to non-bacterial chronic prostatitis, which is generally associated with urogenital pain in the absence of uropathogenic bacteria detected by standard microbiological methodology. Type III prostatitis includes Type IIIA (inflammatory) or IIIB (noninflammatory) prostatitis. These types of prostatitis can be identified by methods known to those of skill in the art including the presence of leukocytes in expressed prostatic secretions or fluids, post prostatic massage urine, or semen (for Type IIIA) or the absence of detectable leukocytes in similar specimens (for Type IIIB). This type of prostatitis can be associated with variable voiding, sexual dysfunction, and/or psychologic alterations.

All of the GenBank Accession numbers listed herein are incorporated by reference as provided on Dec. 14, 2009.

I. Modified Pore Forming Proteins (MPPs)

The modified pore-forming proteins (MPPs) that can be used with the methods of the present disclosure are derived from naturally-occurring pore-forming proteins (nPPs), and have been modified to include one or more prostate-selective modifications such that they are capable of selectively killing prostate cells relative to cells from other normal tissues. Selective killing of prostate cells relative to cells from other tissues is meant that the MPPs are capable of killing prostate cells more effectively than other types of cells such as, for example, lung, spleen, or blood cells. Suitable MPPs include those described in United States Patent Application No. 20040235095 which is hereby incorporated by reference in its entirety.

1. Naturally-Occurring Pore-Forming Proteins (nPPs)

Suitable nPPs from which the MPPs of the present disclosure can be derived include various bacterial toxins that are capable of forming pores or channels in the membrane of a target cell leading to cell death. Suitable bacterial toxins include those that are produced as protoxins and are subsequently activated by proteolytic cleavage as well as those that are produced in an active from and do not require additional processing. In one embodiment, the nPPs are large cytotoxic proteins that are synthesized as protoxins which are activated by protease cleavage at an activation sequence to form pores or channels in the cell membrane of target cells, thus leading to rapid cytolytic cell death.

Suitable nPPs in accordance with this embodiment have the following features: a pore-forming activity that is activated by removal of an inhibitory domain via protease cleavage and the ability to bind to receptors that are present on cell membranes through one or more binding domains. Numerous such nPPs have been cloned and recombinant forms produced (see, for example, Imagawa et al., *FEMS. Microbiol. Lett.* 17: 287-292, 1994; Meza et al. *FEMS Microbiol. Lett.* 145: 333-339, 1996).

In one embodiment, the MPPs are derived from nPPs such as aerolysin or aerolysin-related polypeptides. Examples include, but are not limited to, aerolysin homologues such as proaerolysin from *Aeromonas hydrophila*, *Aeromonas trota* and *Aeromonas salmonicida*, and alpha toxin from *Clostridium septicum* (Ballard et al., *Infect. Immun.* 63: 340-344, 1995; Gordon et al., *J. Biol. Chem.* 274: 27274-27280, 1999; Genbank Accession No. S75954), as well as the following polypeptides: *Bacillus anthracis* protective antigen, *Vibrio cholerae* VCC toxin, epsilon toxin from *Clostridium perfringens*, and *Bacillus thuringiensis* delta toxins (Genbank Accession No. D00117).

Proaerolysin (PA) polypeptides from the *Aeromonas* species noted above have been characterized. These polypeptides exhibit greater than 80% pairwise sequence identity between them (Parker et al., *Progress in Biophysics & Molecular Biology* 88: 91-142, 2005). Each of these PA polypeptides is an approximately 52 kDa protoxin with approximately 470 amino acid residues. The nucleotide and protein sequences for numerous naturally occurring nPPs are known in the art. Non-limiting examples are listed in the following Table:

TABLE 1

Exemplary nPPs and corresponding GenBank™ Accession Numbers

| nPP | Nucleotide sequence (GenBank™ Accession No.) | Amino acid sequence (GenBank™ Accession No.) |
| --- | --- | --- |
| *Aeromonas hydrophila* aerolysin | Buckley AerA, not corrected: M16495 | Buckley AerA corrected P09167 |
| *A. sobria* proaerolysin[1] | Y00559 | CAA68642 |
| *A. sobria* hemolysin[2] | X65046 | CAA46182 |
| *A. trota* proaerolysin[3] | AF064068 | AAC26217 |
| *A. salmonicida* hemolysin[4], | X65048 | CAA46184 |

[1]Husslein et al., *Mol. Microbiol.* 2 (4): 507-517, 1988;
[2]Hirono et al., *Microb. Pathog.* 13 (6): 433-446 (1992);
[3]Kahn et al., *Appl. Environ. Microbiol.* 64 (7): 2473-2478, 1998; and
[4]Hirono et al., *Microb. Pathog.* 15 (4): 269-282, 1993.

The *A. hydrophila* PA protein includes a binding domain (approximately amino acids 1-83) in what is known as the small lobe of the polypeptide and referred to herein as the small lobe binding domain (SBD), and a C-terminal inhibitory peptide (CIP) domain (approximately amino acids 427-470) that is removed by protease cleavage at an activation sequence to activate PA. Cleavage at the activation sequence to remove the CIP domain can be carried out by a number of ubiquitous proteases including furin and trypsin. The amino acid residues from approximately 84-426 are known as the large lobe of the PA polypeptide, and contain a toxin domain and other functional domains, including a second binding domain, referred to herein as the large lobe binding domain (LBD). These and other characteristics of the PA protein are described in WO 06133553, incorporated herein by reference in its entirety.

Alpha toxin from *C. septicum* is considered to be a homologue of proaerolysin based on significant sequence identity and other similarities (Parker et al., supra). These and other characteristics of the alpha toxin are described in WO 06133553.

The activation sequence of *Bacillus thuringiensis* delta-toxin is cleaved by proteases in the midgut of certain insects to produce active endotoxin (Miranda et al., *Insect Biochem. Mol. Biol.* 31: 1155-1163, 2001). These and other characteristics of the delta toxin are described in WO 06133553.

In one embodiment, the MPPs according to the present disclosure are derived from proaerolysin polypeptides, such as proaerolysin polypeptides from *A. hydrophila*. In one particular example, the MPP is derived from a proaerolysin polypeptide with an amino acid sequence provided by SEQ ID NO: 4. In such example, the genetically modified proaerolysin includes a furin recognition and activation sequence at residues 427 to 432 of SEQ ID NO: 2 replaced with a sequence that is recognized and activated by prostate specific antigen (PSA) as shown as residues 427 to 432 of SEQ ID NO: 4. In a further example, an affinity tag is attached to the proaerolysin. For example, a polyhistidine tag, such as a His-tag including 6 histidines is attached to the C or N-terminus of the proaerolysin. In one particular example, the affinity tag is attached to the C-terminal end of the proaerolysin. Without being bound by any particular theory, the addition of 6 histidines (His tag) to the C-terminus of SEQ ID NO: 4 is believed to facilitate purification and enhance expression of the protein. This MMP is known and referred to herein as PRX302 or PSA-PAH1. In other examples, the MPP is a proaerolysin polypeptide that is encoded by a nucleic acid sequence as set forth in SEQ ID NO: 3.

In another embodiment of the disclosure, the MPPs are derived from alpha toxin polypeptides. Alpha toxin from *C. septicum* is considered to be a homologue of proaerolysin based on significant sequence identity and other similarities (Parker et al., supra). Alpha toxin is secreted as a 46,450 Da protoxin (approximately 443 amino acids) that is activated by protease cleavage at an activation sequence to remove a C-terminal inhibitory peptide (CIP) domain, and it also binds to glycosyl-phosphatidylinositol (GPI)-anchored proteins. Alpha toxin, however, does not have a region corresponding to the small lobe of PA. Activation of this polypeptide occurs by protease cleavage at a furin cleavage site (Gordon et al., *Infect. Immun.* 65: 4130-4134, 1997). An example of a *Clostridium septicum* alpha toxin nucleic acid sequence is provided in GenBank™ Accession No. S75954, and an example of a *Clostridium septicum* alpha toxin protein sequence is provided in GenBank™ Accession No. AAB32892. Based on the sequence homology, alpha toxin is thought to have a similar structure and similar ability to bind to GPI-anchored proteins.

In additional embodiments, the MPPs are derived from nPPs that do not require protease cleavage for activation, and thus do not have an activation sequence. These nPPs can be modified to insert a prostate-specific protease cleavage site into the nPP resulting in an MPP that is capable of being selectively activated to kill prostate cells. Examples of such nPPs include *Staphylococcus aureus* γ-hemolysin. In the case of this nPP, an activation sequence can be inserted into the center of the pore-forming domain as is known in the art (Panchal et al., *Nat. Biotech.* 14: 852-856, 1996).

The present disclosure further includes MPPs that are derived from biologically active fragments of nPPs. Biologically active fragments of nPPs are those that are capable of forming pores and killing cells. Suitable fragments include those that are capable of being activated to form pores in target cells by removal of a CIP domain. For example, in the case of PA, a suitable fragment would be one that included a binding domain of the protein as well as the CIP domain and activation sequence. Thus, in one embodiment of the disclosure, the MPP is derived from a fragment of proaerolysin that includes a binding domain, the CIP domain and the activation sequence. In another embodiment, the MPP is derived from a fragment of proaerolysin that includes the binding domain, the activation sequence, but only part of a CIP domain.

2. Prostate-Specific Modifications

In accordance with the present disclosure, the selected nPP is modified to form a MPP by inclusion of one or more prostate-specific modifications. Exemplary prostate-specific modifications include incorporation of a prostate-specific activation sequence, functional deletion (including functional replacement) of one or more binding domains, addition of a prostate-specific targeting domain, or combinations thereof.

In one embodiment, the MPP includes a prostate-specific activation sequence that allows for selective activation of the MPP in prostate cells. A prostate-specific activation sequence may be generated by modification of the naturally occurring activation sequence of a nPP, or it may be generated by the addition of a prostate-specific activation sequence to a nPP that does not have a naturally-occurring activation sequence. In another embodiment, the MPPs include a prostate-specific activation sequence and one or more prostate-specific targeting domains. In another embodiment, the MPPs include a prostate-specific activation sequence and a modification to the SBD. In another embodiment, the MPPs include a prostate-specific activation sequence and a modification to the LBD.

In one embodiment, the MPPs include one or more prostate-specific targeting domains that allow for selective activation of the MPPs in prostate cells. In another embodiment, the MPPs include one or more prostate-specific targeting domain and a modification to the SBD. In another embodiment, the MPPs include a prostate-specific targeting domain and a modification to the LBD.

In still another embodiment, the MPPs include a prostate-specific activation sequence, one or more prostate-specific targeting domain and a modification to the LBD. In another embodiment, the MPPs include a prostate-specific activation sequence, one or more prostate-specific targeting domains, and a modification to the SBD.

In one embodiment, the MPP includes a prostate-specific activation sequence and one or more modifications to the native binding domain. In another embodiment, the MPP includes a prostate-specific targeting domain and one or more modifications to the native binding domain. In still another embodiment, the MPP includes a prostate-specific activation sequence, a prostate-specific targeting domain, and one or more modifications to the native binding domain.

Representative, non-limiting examples of combinations of prostate-specific modifications that can be made to proaerolysin are disclosed in WO 06133553, incorporated herein by reference in its entirety.

Modification of Activation Sequence

As indicated above, a nPP can be modified to incorporate a prostate-specific activation sequence by modification of the naturally occurring activation sequence to provide a prostate-specific activation sequence, or a prostate-specific activation sequence can be added to an nPP that does not have a naturally occurring activation sequence. A prostate-specific activation sequence in accordance with the present disclosure is a sequence of amino acids that incorporates one or more prostate-specific protease cleavage sites. A prostate-specific protease cleavage site is a sequence of amino acids that is recognized and selectively and efficiently hydrolyzed (cleaved) by a prostate-specific protease. In one embodiment, a prostate-specific protease is a protease that is expressed at higher levels in prostate cells than in other cell types. Examples of prostate-specific proteases include, but are not limited to: PSA (prostate-specific antigen), PSMA (prostate-specific membrane antigen), and HK2 (human glandular kallikrein 2) cleavage sequences. Numerous examples of cleavage sites recognized by these prostate-specific proteases are known in the art.

Modifications to a naturally-occurring activation sequence to provide a prostate-specific protease activation sequence can be generated using methods known in the art. Modification of the naturally occurring activation sequence results in functional deletion of the native activation sequence. Functional deletion can be achieved by mutation, partial or complete deletion, insertion, or other variation made to the naturally occurring activation sequence that renders it inactive.

In one embodiment, the naturally-occurring activation sequence of the nPP is functionally deleted by insertion of a prostate-specific activation sequence. In another embodiment, functional deletion of the naturally occurring activation sequence is achieved via mutations in one or more amino acid residues of the native activation sequence which produce a prostate-specific activation sequence. In an alternate embodiment, the naturally occurring activation sequence of the nPP is functionally deleted by replacing the native protease cleavage site of the activation sequence with a prostate-specific protease cleavage site.

In one embodiment, the one or more prostate-specific protease cleavage sites functionally replace the native protease cleavage site of the MPP. For example, a prostate-specific protease cleavage site can functionally replace the native furin cleavage site of PA. This replacement results in a MPP that becomes cytolytically active in the presence of an enzymatically active prostate-specific protease, such as PSA, PSMA, or HK2. Suitable PSA, PSMA, or HK2 cleavage sites are known in the art and are described in WO 06133553 which is incorporated by reference in its entirety.

In another embodiment, MPPs can be generated by deleting the native protease cleavage site of the nPP and inserting a prostate-specific activation sequence. For example the furin cleavage site of PA (amino acids 427-432) can be deleted and a prostate-specific protease cleavage site, such as a PSA cleavage site inserted therein.

In a further embodiment, the native protease cleavage site of the nPP is mutated such that it is no longer functional and a prostate-specific activation sequence is inserted within the mutated protease cleavage site, or added to the N- or C-terminus of the native protease cleavage site. For example, the furin cleavage site of PA can be mutated and a prostate-specific protease cleavage site, such as a PSA cleavage site, inserted within, or added to the N- or C-terminus of the mutated furin site.

In still another embodiment, a prostate-specific activation sequence is added to an nPP that does not have a naturally occurring activation sequence. For example, *Staphylococcus aureus* α-hemolysin, which does not require protease cleavage in order to be activated to kill cells, may be engineered to include one or more prostate-specific protease cleavage sites, thus rendering it capable of being selectively activated to kill prostate cells.

Prostate-Specific Cleavage Sites

As noted above, various prostate-specific proteases and the protease cleavage sites they recognize are known in the art. Examples include, but are not limited to, PSA, PSMA and HK2. In one embodiment, the MPP is modified to include a prostate-specific activation sequence that includes a PSA-specific cleavage site. A PSA-specific cleavage site is a sequence of amino acids which is recognized and selectively and efficiently hydrolyzed (cleaved) by prostate specific antigen (PSA). PSA is a serine protease with the ability to recognize and hydrolyze specific peptide sequences. It is secreted by prostate cells in an enzymatically active form and becomes inactivated upon entering the circulation. Since neither blood nor normal tissue other than the prostate contains enzymatically active PSA, the proteolytic activity of PSA can be used to activate MPPs at the prostate gland.

Various PSA-specific cleavage sites are known in the art. Examples, include, but are not limited to, those disclosed in U.S. Pat. Nos. 5,866,679, 5,948,750, 5,998,362, 6,265,540, 6,368,598, and 6,391,305.

Additional PSA-specific cleavage sites are known, based on the PSA-cleavage map of human seminal proteins semenogelin I and 11, and a cellulose membrane based assay (see Denmeade et al., *Cancer Res.*, 57: 4924-4930, 1997) and can be used to produce modified MPPs. For example, the MPPs can be modified to include one of the PSA-cleavage sites, which can substitute for the wild-type furin protease activation site of proaerolysin (amino acids 427-432), as is known in the art.

In one embodiment, the MPP has an amino acid sequence which includes an activation sequence containing a PSA cleavage site. In another embodiment, the MPP includes a prostate-specific activation sequence that includes a PSMA-specific cleavage site. Examples of suitable PSMA-specific cleavage sites are known in the art and can be found, for example, in International Publication No. WO 02/43773, which is incorporated by reference in its entirety. In general terms, a PSMA cleavage site includes at least the dipeptide $X_1X_2$. The dipeptide contains the amino acids Glu or Asp at position $X_1$. $X_2$ can be Glu, Asp, Gln, or Asn. Tripeptides $X_1X_2X_3$ are also suitable, with $X_1$ and $X_2$ defined as before, with $X_3$ as Glu, Asp, Gln or Asn. Tetrapeptides $X_1X_2X_3X_4$ are also suitable, with $X_{1-3}$ defined as above, and with $X_4$ as Glu, Asp, Gln or Asn. Pentapeptides $X_1X_2X_3X_4X_5$ are also suitable, with $X_{1-4}$ defined as above, and with $X_5$ as Glu, Asp, Gln or Asn. Hexapeptides $X_1X_2X_3X_4X_5X_6$ are also suitable, with $X_{1-5}$ defined as above, and with $X_6$ as Glu, Asp, Gln or Asn. Further peptides of longer sequence length can be constructed in similar fashion. Generally, the peptides are of the following sequence: $X_1 \ldots X_n$, where n is 2 to 30, 2 to 20, 2 to 15, or 2 to 6, where $X_1$ is Glu, Asp, Gln or Asn. In one embodiment, $X_1$ is Glu or Asp, and $X_2$-$X_n$ are independently selected from Glu, Asp, Gln and Asn. Other possible peptide sequences are as above, except that $X_2$-$X_{n-1}$ are independently selected from Glu, and Asp, and $X_n$ is independently selected from Glu, Asp, Gln and Asn. Examples of PSMA cleavage sites are Asp-Glu, Asp-Asp, Asp-Asn, Asp-Gln, Glu-Glu-Glu, Glu-Asp-Glu, Asp-Glu-Glu, Glu-Glu-Asp, Glu-Asp-Asp, Asp-Glu-Asp, Asp-Asp-Glu, Asp-Asp-Asp, Glu-Glu-Gln, Glu-Asp-Gln, Asp-Glu-Gln, Glu-Glu-Asn, Glu-Asp-Asn, Asp-Glu-Asn, Asp-Asp-Gln, and Asp-Asp-Asn.

In an additional embodiment, the MPP includes a prostate-specific activation sequence that includes an HK2-specific cleavage site. Examples of HK2-specific cleavage sites are also known in the art and described, for example, in International Publication No. WO 01/09165, which is hereby incorporated by reference in its entirety. The cleavage site recognized by HK2 is flanked by at least an amino acid sequence $X_4X_3X_2X_1$. This amino acid sequence contains the amino acid arginine, histidine or lysine at position $X_1$. $X_2$ can be arginine, phenylalanine, lysine, or histidine. $X_3$ can be lysine, serine, alanine, histidine or glutamine. $X_4$ can be from 0 to 20 further amino acids, and can be at least two further amino acids. In an embodiment, the HK2 cleavage site includes a sequence for $X_4$ that is substantially identical to the 20 amino acids in the wild type semenogelin I or semenogelin II sequence that are the from fourth to twenty fourth amino acids to the N-terminal side of recognized semenogelin cleavage sites. The amino acid sequence can further include $X_{-1}$, which is linked to the carboxy terminus of $X_1$ to create the amino acid sequence $X_4X_3X_2X_1X_{-1}$. $X_{-1}$ is up to a further 10 amino acids, and can include various amino acids. $X_{-1}$ may have a leucine, alanine or serine linked to the carboxy terminus of $X_1$. $X_{-1}$ can include L- or D-amino acids. The HK2 cleavage site is located at the carboxy terminal side of $X_1$.

Addition of Prostate-Specific Targeting Domain

In one embodiment, MPPs include one or more prostate-specific targeting domains to allow selective targeting of prostate cells. The prostate-specific targeting domain is capable of directing the MPP to the prostate cell, where the MPP can be activated and subsequently kill the prostate cell. The targeting domain can be located at the N- or C-terminus of the MPP, or both. Alternatively, the targeting domain can located at another region of the MPP, as long as it does not interfere with the pore-forming activity of the MPP.

Examples of suitable prostate-specific targeting domains include, but are not limited to molecules such as a peptide ligand, toxin, or antibody, which have a higher specificity for prostate cells than for other cell types. In one embodiment, a prostate tissue specific binding domain has a lower $K_D$ in prostate tissue or cells than in other cell types, (i.e., binds selectively to prostate tissues as compared to other normal tissues), for example at least a 10-fold lower $K_D$, such as an at least 20-, 50-, 75-, 100- or even 200-fold lower $K_D$. Such molecules can be used to target a MPP to the prostate. Examples include, but are not limited to: antibodies which recognize proteins that are relatively prostate-specific such as PSA, PSMA, HK2, prostasin, and hepsin; ligands which have prostate-specific receptors such as natural and synthetic luteinizing hormone releasing hormone (LHRH); and endothelin (binding to cognate endothelin receptor).

In one embodiment, addition of the prostate-specific targeting domain results in functional deletion of the native binding domain of the nPP. In another embodiment, the native non-specific GPI-anchor protein binding domain of proaerolysin is functionally deleted and replaced with a prostate-specific targeting domain.

One or more prostate tissue-specific binding domains can be linked to one or more amino acids of the MPPs, but ideally, do not interfere significantly with the ability to form pores in cell membranes, or, where applicable, with the ability of the MPP to be activated by a prostate-specific protease such as PSA. Methods of conjugating proteins or peptides to MPPs are known in the art and include for example, changing the N-terminal amino acid of the protein to be modified to a Cys or other amino acid before attaching the prostate-tissue specific binding domain, to assist in linking the prostate-tissue specific binding domain to the MPP.

In one embodiment, prostate tissue specific binding domains are linked or inserted at the N- and/or C-terminus of an MPP derived from proaerolysin. In some examples, the native binding domain of proaerolysin is deleted. In other examples, smaller deletions or point mutations are introduced into the native binding domain of proaerolysin.

Antibodies as Prostate-Specific Targeting Domains

In one embodiment, the prostate specific targeting domain is an antibody or antibody fragment that specifically binds to an antigen that is associated with prostate cells, thus targeting the MPP to prostate cells. Antigens associated with prostate cells that may be specifically bound by such prostate-specific targeting domains include PSA, and PSMA and the LHRH receptor, the expression of which is elevated in prostate cells. Antibodies can be attached to the N- or C-terminus of the MPP using gene fusion methods well known in the art (for example see Debinski and Pastan, *Clin. Cancer Res.* 1:1015-22, 1995). Alternatively, antibodies can be attached to an MPP by covalent crosslinking (for example see Woo et al., *Arch. Pharm. Res.* 22(5):459-63, 1999 and Debinski and Pastan, *Clin. Cancer Res.* 1(9):1015-22, 1995). Crosslinking can be non-specific, for example by using a homobifunctional-lysine-reactive crosslinking agent, or it can be specific, for example by using a crosslinking agent that reacts with amino groups on the antibody and with cysteine residues located in the MPP. In one embodiment, proaerolysin amino acids such as amino acids Cys19, Cys75, Cys159, and/or Cys164 of SEQ ID NO: 2 can be used to crosslink antibodies to the modified proaerolysin molecule. For example, the antibody could replace the native binding domain of the nPP to be modified, or the antibody could be added to an MPP already having mutations in the native binding domain. Such an MPP can also include a prostate-specific activation sequence to increase specificity. In one embodiment, the antibody is a single chain antibody to PSMA fused to the toxin domain of PA.

Suitable antibodies include intact antibodies as well as antibody fragments such as, for example, (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., *Nature* 341:544-6, 1989) which consists of a VH domain; (v) an isolated complementarity determining region (CDR); and (vi) an F(ab')2 fragment, a bivalent fragment comprising two Fab fragments linked by a disulfide bridge at the hinge region. Suitable antibodies include single chain Fv antibodies, which are prepared by recombinant methods resulting in the two domains of an Fv fragment being linked via a synthetic linker (Bird et al., *Science* 242:423-6, 1988; and Huston et al., *Proc. Natl. Acad. Sci.* 85:5879-83, 1988), and camelized antibodies (for example see Tanha et al., *J. Biol. Chem.* 276:24774-80, 2001).

In another embodiment, the antibody fragments are capable of crosslinking their target antigen, e.g., bivalent fragments such as F(ab')2 fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques and the fragments screened for utility in the same manner as described for whole antibodies, and as is known in the art. An antibody is further intended to include nanobodies, and bispecific and chimeric molecules that specifically bind the target antigen.

"Specifically binds," when used in reference to an antibody, refers to the ability of individual antibodies to specifically immunoreact with a specific antigen. The binding is a non-random binding reaction between an antibody molecule and an antigenic determinant of the antigen. The desired binding specificity is typically determined from the reference point of the ability of the antibody to differentially bind the specific and an unrelated antigen, and therefore distinguish between two different antigens, particularly where the two antigens have unique epitopes. An antibody that specifically binds to a particular epitope is referred to as a "specific antibody".

Small Peptide Ligands as Prostate-Specific Targeting Domains

In one embodiment, the prostate-specific targeting domain is a small peptide ligand that binds to its cognate prostate-specific receptor expressed on the membrane of prostate cells. Examples include, but are not limited to natural and synthetic luteinizing hormone releasing hormone (LHRH) agonist peptides (for example see Genbank Accession No. CAA25526), which bind with high affinity to LHRH receptors, and peptides that can bind selectively to PSMA. LHRH receptors are displayed by prostate cells, and only a few other cells. This differential expression provides binding specificity.

Small peptide ligands may be modified as is known in the art in order to facilitate their attachment to the MPP. For example, certain residues of LHRH, such as the Gly at the 6th position (Gly6), can be substituted without compromising receptor binding affinity (Janaky et al., *Proc. Natl. Acad. Sci. USA* 89: 972-976, 1992; Nechushtan et al., *J. Biol. Chem.,* 272: 11597-11603, 1997). Therefore, an MPP (in which the native binding domain is functionally deleted) can be produced which is covalently coupled to purified LHRH D-Lys6 (at the epsilon amine of this lysine).

LHRH D-Lys6 can be attached at various positions within an nPP to provide an MPP having a prostate-specific targeting domain. As noted above, attachment of the small peptide ligand will not significantly interfere with the ability of the toxin to insert into the membrane to form a pore. For example, the epsilon amine of the D-Lys6 analog can be coupled to the amino terminus of the MPP using methods known in the art such as for example via a dicarboxylic acid linker. Activation of the MPP by cleavage of the activation sequence will result in release of the C-terminal inhibitory portion while the toxin remains bound to the LHRH receptor.

Alternatively or in addition, the small peptide ligand can be coupled directly to the C-terminus of the MPP. For example, the epsilon amine of the D-Lys6 analog of LHRH can be coupled directly to the C-terminal carboxyl of the MPP by the addition of a Cys to the C-terminus of the MPP, then crosslinking this Cys to the epsilon amine of the D-Lys6 analog of LHRH. This coupling will produce an MPP in which the LHRH peptide is attached to the C-terminal inhibitory domain. Activation of the MPP by cleavage of the activation sequence will liberate the MPP and leave the inhibitory fragment bound to the LHRH receptor. In addition, recombinant fusion proteins can be produced in which modified LHRH peptides are fused to both the N- and C-terminus of the MPP.

It is also contemplated that the small peptide ligand may be attached to an MPP via a disulfide bridge. For example, a cysteine residue is introduced into the 6th position of the LHRH peptide and the peptide attached to an MPP via a disulfide bridge. The cysteine with which the peptide forms a disulphide bridge can be present in the native nPP sequence or the nPP can be mutated to include a cysteine residue. In one embodiment, an MPP derived from PA can have a cysteine residue introduced, for example at amino acids 215 and/or 300 of SEQ ID NO: 2, wherein amino acid 215 and/or 300 has been mutated to a cysteine.

In another embodiment, a recombinant protein is produced in which LHRH peptide is fused to the amino terminus of the MPP. Alternatively or in addition, an MPP may be produced by attaching or linking one or more prostate-specific targeting domains to other amino acids of the MPP. For example, for MPPs derived from proaerolysin, amino acids such as amino acid 215 or 300 of SEQ ID NO: 2 or 4 may be used to attach the one or more prostate specific targeting domains. In some examples, a Cys amino acid replaces the native amino acid at that position. For example, the following changes can be made to SEQ ID NO: 2 or 4: Tyr215Cys or Ala300Cys. Alternatively, cysteine residues present in the native sequence of the nPP can be utilized. For MPPs derived from proaerolysin, amino acids such as amino acids Cys19, Cys75, Cys159, and/or Cys164 of SEQ ID NO: 2, are suitable for this purpose.

Modifications to the Native Binding Domain of MPPs

MPPs that can be used with the disclosed methods can be derived from nPPs that include one or more binding domains, as known in the art. In the context of the present disclosure, when an nPP includes one binding domain, it is considered to be a "large lobe binding domain." MPPs according to the present disclosure may include modifications to one or more binding domains, as applicable. For example, native proaerolysin from *Aeromonas* species includes two binding domains, a small lobe binding domain, and a large lobe binding domain. In contrast, native alpha toxin from *Clostridium septicum* includes only a large lobe binding domain. In one embodiment, modifications of the binding domains include functional deletion of a binding domain. A functionally deleted binding domain in an MPP results in an MPP that has an attenuated ability to bind to its cell surface receptor, yet still retains pore-forming ability.

Functional deletions can be made by deleting or mutating one or more binding domains of an MPP. In one embodiment, the entire binding domain or portions thereof, may be deleted. In an additional embodiment, insertion of heterologous sequences into the binding domain may also be used to functionally delete the binding domain. Addition of these heterologous sequences may confer an additional functionality to the MPP (i.e., functional replacement of the binding domain). For example, addition of a heterologous sequence can result in the addition of a region that can function as a prostate-specific targeting domain as described herein. In still another embodiment, point mutations to the amino acid sequence of the native binding domain of the nPP can also be made to decrease the ability of the binding domain to bind to its receptor. Further details regarding these modifications are described below.

MPPs lacking a binding domain retain their cytolytic activity, but may need to be administered at higher doses to ensure concentration of the toxin in the cell membrane. MPPs with functional deletions in the binding domain may be prepared using methods known in the art. These methods include the use of recombinant DNA technology as described in Sambrook et al., supra. Alternatively, functional deletions of the binding domain may also be achieved by direct modification of the protein itself according to methods known in the art, such as proteolysis to generate fragments of the MPP, which can then be chemically linked together.

In one embodiment, the MPP is modified by functional deletion of its small lobe binding domain (SBD). Exemplary functional deletions of the SBD may be made in the *A. hydrophila* proaerolysin polypeptide as follows. The entire SBD, corresponding to amino acid 1-83 of SEQ ID NO: 2 may be deleted, or portions of this region may be deleted, for example amino acids 45-66 of SEQ ID NO: 2. Alternatively, point mutations can be made as follows W45A, 147E, M57A, Y61A, K66Q (amino acid numbers refer to SEQ ID NO: 2 or SEQ ID NO: 4) and as described in Mackenzie et al. *J. Biol. Chem.* 274: 22604-22609, 1999.

In one embodiment, the nPP is modified by functional deletion of its large lobe binding domain (LBD). Exemplary functional deletions of the LBD of proaerolysin (contained in approximately amino acid residues 84-426 of SEQ ID NO: 2) that may be made to provide MPPs are as follows. The entire LBD of proaerolysin may be deleted. Alternatively, the MPP derived from proaerolysin includes one or more point mutations in the LBD to amino acid residues Y162, W324, R323, R336, and/or W127. In another embodiment of the disclosure, the MPP derived from proaerolysin includes one or more point mutations at positions W127 and/or R336. In still another embodiment, the MPP derived from proaerolysin includes the point mutations Y162A and/or W324A. In a further embodiment the MPP derived from proaerolysin includes the point mutations R336A, R336C, and/or W127T. In another embodiment, MPPs include mutations to other residues that interact directly with the GPI-protein ligand.

Further Modifications of MPPs

The present disclosure contemplates further modification of MPPs that do not affect the ability of the MPPs to selectively target prostate cells. Such modifications include amino acid substitutions, insertions or deletions, modifications to reduce antigenicity, and modifications to enhance the stability or improve the pharmacokinetics of the MPPs. In one embodiment, further modifications to MPPs result in a polypeptide that differs by only a small number of amino acids from the MPP. Such modifications include deletions (for example of 1-3 or more amino acids), insertions (for example of 1-3 or more residues), or substitutions that do not interfere with the ability of the MPPs to selectively target and kill normal prostate cells. In one embodiment, further modifications to the MPPs result in a polypeptide that retains at least 70%, 80%, 85%, 90%, 95%, 98%, or greater sequence identity to the MPP (such as SEQ ID NO: 3 or 4) and maintains the ability of the MPP to selectively target and kill normal prostate cells.

MPPs may be modified by substitution whereby at least one residue in the amino acid sequence has been removed and a different residue inserted in its place. In one embodiment, the substitution is a conservative substitution. A conservative substitution is one in which one or more amino acids (for example 2, 5 or 10 residues) are substituted with amino acid residues having similar biochemical properties. Typically, conservative substitutions have little to no impact on the activity of a resulting polypeptide. For example, ideally, an MPP including one or more conservative substitutions retains the activity of the corresponding nPP. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met;

Met, Leu or Tyr for Phe; Thr for Ser; Ser for Thr; Tyr for Trp; Trp or Phe for Tyr; and Ile or Leu for Val.

An MPP can be modified to include one or more conservative substitutions by manipulating the nucleotide sequence that encodes that polypeptide using, for example, standard procedures such as site-directed mutagenesis or PCR. Further information about conservative substitutions can be found in, among other locations, Ben-Bassat et al., (*J. Bacteriol.* 169: 751-757, 1987), O'Regan et al., (*Gene* 77: 237-251, 1989), Sahin-Toth et al., (*Protein Sci.* 3: 240-247, 1994), Hochuli et al., (*BioTechnology* 6: 1321-1325, 1988), WO 00/67796 (Curd et al.) and in standard textbooks of genetics and molecular biology.

In another embodiment the substitution is a permissive substitution. Permissive substitutions are non-conservative amino acid substitutions, but also do not significantly alter MPP activity. An example is substitution of Cys for Ala at position 300 of SEQ ID NO: 2 or 4 in a proaerolysin polypeptide. In one embodiment, MPPs are modified to include one or more amino acid substitutions of single residues. In another embodiment, the MPPs are modified to include one amino acid substitution. In another embodiment, the MPPs are modified to include from about 2 to about 10 amino acid substitutions. In another embodiment, the MPPs are modified to include about 3 to about 5 amino acid substitutions.

Non-limiting examples of further modifications to MPPs derived from proaerolysin are listed in Table 2. Similar mutations can be made to SEQ ID NO: 4.

TABLE 2

Exemplary single mutations of MPPs derived from a native proaerolysin polypeptide (SEQ ID NO: 2)

| H107N | G202C | G251C | T284C | H341N |
|---|---|---|---|---|
| K22C | H121N | W203C | E252C | V285C |
| W127T | T253S | V293C | K361C | N459C |
| C164S | D216C | T253C | K294C | K369Q |
| Q254C | K294Q | W371L | D372N | I445C |
| Y135A | R220Q | E296C | K299C | K349C |
| Y135F | K171C | K238C | W373L | A418C |
| K22C | A300C | S256C | K309C | H332N |
| H186N | P248C | E258C | I416C | Q263C |
| K198C | L249C | I259C | G417C | |
| K114C | C159S | V201C | V250C | |

Peptidomimetic and organomimetic embodiments are also contemplated, whereby the three-dimensional arrangement of the chemical constituents of such peptido- and organomimetics mimic the three-dimensional arrangement of the polypeptide backbone and component amino acid side chains in the polypeptide, resulting in such peptido- and organomimetics of an MPP which have the ability to lyse prostate cells. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* (ed. Munson, 1995), chapter 102 for a description of techniques used in CADD.

Other modifications that may be made to the MPPs include, for example, modifications to the carboxylic acid groups of the MPP, whether carboxyl-terminal or side chain, in which these groups are in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the polypeptide, whether amino-terminal or side chain, can be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Other modifications include conversion of hydroxyl groups of the polypeptide side chain to $C_1$-$C_{16}$ alkoxy or to a $C_1$-$C_{16}$ ester using well-recognized techniques. Phenyl and phenolic rings of the polypeptide side chain can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides described herein to select and provide conformational constraints to the structure that result in enhanced stability. For example, a carboxyl-terminal or amino-terminal cysteine residue can be added to the polypeptide, so that when oxidized the polypeptide will contain a disulfide bond, generating a cyclic peptide. Other peptide cyclizing methods include the formation of thioethers and carboxyl- and amino-terminal amides and esters.

The present disclosure also contemplates further modifications to MPPs in which the MPPs are linked or immobilized to a surface, such as a bead. The bead can also include a prostate-specific ligand to enhance targeting to a prostate cell. Immobilized refers to binding to a surface, such as a solid surface. A solid surface can be polymeric, such as polystyrene or polypropylene. The solid surface may be in the form of a bead. In one embodiment, the surface includes an immobilized MPP, and in other embodiments further includes one or more prostate-specific binding ligands, such as LHRH peptide, PSMA antibody, and PSMA single chain antibody. In another embodiment, the MPP is liberated from the bead once the bead reaches the prostate cell target. Methods of immobilizing peptides on a solid surface are known in the art and can be found in WO 94/29436, and U.S. Pat. No. 5,858,358.

The present disclosure further contemplates that the MPP can include further modifications intended to improve the pharmacokinetic properties of the molecule when administered to a subject. Various modifications to reduce immunogenicity and/or improve the half-life of therapeutic proteins are known in the art. For example, the MMPs can undergo glycosylation, isomerization, or deglycosylation according to standard methods known in the art. Similarly, the MPP can be modified by non-naturally occurring covalent modification for example by addition of polyethylene glycol moieties (pegylation) or lipidation. In one embodiment, the MPP is conjugated to polyethylene glycol (PEGylated) to improve their pharmacokinetic profiles. Conjugation can be carried out by techniques known to those skilled in the art (see, for example, Deckert et al., *Int. J. Cancer* 87: 382-390, 2000; Knight et al., *Platelets* 15: 409-418, 2004; Leong et al., *Cytokine* 16: 106-119, 2001; and Yang et al., *Protein Eng.* 16: 761-770, 2003). In one embodiment, antigenic epitopes can be identified and altered by mutagenesis. Methods of identifying antigenic epitopes are known in the art (see for example, Sette et al., *Biologicals* 29: 271-276), as are methods of mutating such antigenic epitopes.

II. Pharmaceutical Compositions

The present disclosure provides pharmaceutical compositions comprising an MPP and one or more non-toxic pharmaceutically acceptable carriers, diluents, excipients and/or adjuvants, which can be used with the disclosed methods for treating prostatitis. If desired, other active ingredients may be included in the compositions. Examples of other therapeutics that can be administered in combination with one or more MMPs include but not limited to alpha-blocker therapy (for obstructive voiding), anti-inflammatory agents, antibiotics, alterations in lifestyle such as diet (such as the reduction of the intake of caffeine), exercise, sexual activity, and/or supportive psychotherapy or "coping mechanisms". In one example, the MMP is not administered in combination with an antibiotic.

The pharmaceutical compositions may include from about 1% to about 95% of an MPP. Compositions formulated for administration in a single dose form may include, for example, about 20% to about 90% of the MPP, whereas compositions that are not in a single dose form may include, for example, from about 5% to about 20% of the MPP. Concentration of the MPP in the final formulation can be as low as 0.01 μg/mL. For example, the concentration in the final formulation can be between about 0.01 μg/mL and about 1,000 μg/mL. In one embodiment, the concentration in the final formulation is between about 0.01 μg/mL and about 100 μg/mL. Non-limiting examples of unit dose forms include dragees, tablets, ampoules, vials, suppositories and capsules.

In an embodiment, a pharmaceutical composition includes a MPP with an amino acid sequence set forth by SEQ ID NO: 4, and in some examples SEQ ID NO: 4 with a polyhistidine tag (6-His) at the C-terminus. Examples of effective iv doses of such composition for a 70 kg human are about 1-10 mg of the MPP, for example about 1-5 mg, for example about 1-3 mg, for example about 2.8 mg. Examples of effective intraprostatic doses of the MPP for a 70 kg human are about 10-100 mg of modified PA toxin, for example about 10-50 mg, for example about 10-30 mg, for example about 28 mg.

In an example in which a nucleic acid is employed to allow expression of a nucleic acid in a cell, the nucleic acid is delivered intracellularly (e.g., by expression from a nucleic acid vector or by receptor-mediated mechanisms). In one embodiment, a nucleic acid encodes for a MPP with an amino acid as set forth by SEQ ID NO: 4, such as the nucleic acid sequence of SEQ ID NO: 3 (which can include additional nucleotides, for example sequence at the 5'-end that encodes six histadine residues).

Various delivery systems for administering a nucleic acid or protein are known, and include encapsulation in liposomes, microparticles, microcapsules, receptor-mediated endocytosis (Wu and Wu, *J. Biol. Chem.* 262: 4429-4432, 1987), and construction of therapeutic nucleic acids as part of a retroviral or other vector. Methods of introduction include, but are not limited to, intraprostatic, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal, vaginal and intestinal mucosa, etc.) and may be administered together with other biologically active agents. Administration can be systemic or local.

Liposomes fuse with the target site and deliver the contents of the lumen intracellularly. The liposomes are maintained in contact with the target cells for a sufficient time for fusion to occur, using various means to maintain contact, such as isolation and binding agents. Liposomes can be prepared with purified proteins that mediate fusion of membranes, such as Sendai virus or influenza virus. The lipids may be any useful combination of known liposome forming lipids, including cationic lipids, such as phosphatidylcholine. Other potential lipids include neutral lipids, such as cholesterol, phosphatidyl serine, phosphatidyl glycerol, and the like. For preparing the liposomes, the procedure described by Kato et al. (*J. Biol. Chem.,* 266: 3361, 1991) can be used.

Where the therapeutic molecule is a nucleic acid, administration can be achieved by an appropriate nucleic acid expression vector which is administered so that it becomes intracellular, e.g., by use of a retroviral vector (see U.S. Pat. No. 4,980,286), or by direct injection, or by use of microparticle bombardment (e.g., a gene gun), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 88: 1864-1868, 1999), etc. Alternatively, the nucleic acid can be introduced intracellularly and incorporated within host cell DNA for expression, by homologous recombination.

The vector pcDNA, is an example of a method of introducing the foreign cDNA into a cell under the control of a strong viral promoter (CMV) to drive the expression. However, other vectors can be used (such as pRETRO-ON, Clontech), which also use this promoter but have the advantages of entering cells without any transfection aid, integrating into the genome of target cells only when the target cell is dividing and they are regulated. It is also possible to turn on the expression of a nucleic acid by administering tetracycline when these plasmids are used. Other plasmid vectors, such as pMAM-neo (Clontech) or pMSG (Pharmacia) use the MMTV-LTR promoter (which can be regulated with steroids) or the SV10 late promoter (pSVL, Pharmacia) or metallothionein-responsive promoter (pBPV, Pharmacia) and other viral vectors, including retroviruses. Examples of other viral vectors include adenovirus, AAV (adeno-associated virus), recombinant HSV, poxviruses (vaccinia) and recombinant lentivirus (such as HIV). These vectors achieve the basic goal of delivering into the target cell the cDNA sequence and control elements needed for transcription. The present disclosure includes all forms of nucleic acid delivery, including synthetic oligos, naked DNA, plasmid and viral, integrated into the genome or not.

The composition can be a liquid solution, suspension, emulsion, tablet, pill, capsule, sustained release formulation, or powder. For solid compositions (e.g., powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

For administration to an animal or human, the pharmaceutical compositions can be formulated for administration by a variety of routes. For example, the compositions can be formulated for oral, topical, transrectal, transurethral, transperineal, intraprostatic, or parenteral administration or for administration by inhalation or spray. The term parenteral as used herein includes subcutaneous injections, intravenous, intramuscular, intrathecal, intrasternal injection or infusion techniques. Direct injection or infusion into the prostate gland via image guidance such as transrectal ultrasound is also contemplated. Convection enhanced delivery, a standard administration technique for protein toxins, is also contemplated by the present disclosure. Formulations can also include one or more viscosity enhancing agents which act to prevent backflow of the formulation when it is administered, for example by injection or via catheter. Such viscosity enhancing agents include, but are not limited to, biocompatible glycols and sucrose The MPPs can be delivered along with a pharmaceutically acceptable vehicle. Such a vehicle may enhance the stability and/or delivery properties. Thus, the present disclosure also provides for formulation of the MPP with a suitable vehicle, such as an artificial membrane vesicle (including a liposome, noisome, nanosome and the like), microparticle or microcapsule, or as a colloidal formulation that includes a pharmaceutically acceptable polymer. The use of such vehicles/polymers may be beneficial in achieving sustained release of the MPPs. Alternatively, or in addition, the MPP formulations can include additives to stabilize the protein in vivo, including stabilizers for protein therapeutics known in the art.

Pharmaceutical compositions for oral use can be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavoring agents, coloring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatin or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monostearate or glyceryl distearate may be employed.

Pharmaceutical compositions for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium such as peanut oil, liquid paraffin or olive oil.

Pharmaceutical compositions formulated as aqueous suspensions contain the active compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-α-cyclodextrin, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, one or more colouring agents, one or more flavoring agents or one or more sweetening agents, such as sucrose or saccharin.

Pharmaceutical compositions can be formulated as oily suspensions by suspending the active compound(s) in a vegetable oil, for example, *arachis* oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavoring agents may be added to provide palatable oral preparations. These compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the active ingredient in admixture with one or more dispersing or wetting agents, suspending agents and/or preservatives. Suitable dispersing or wetting agents and suspending agents are exemplified by those already mentioned above. Additional excipients, for example, sweetening, flavoring and coloring agents, can also be included in these compositions.

Pharmaceutical compositions of this disclosure can also be formulated as oil-in-water emulsions. The oil phase can be a vegetable oil, for example, olive oil or *arachis* oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions can also optionally contain sweetening and flavoring agents.

Pharmaceutical compositions can be formulated as a syrup or elixir by combining the active ingredient(s) with one or more sweetening agents, for example glycerol, propylene glycol, sorbitol or sucrose. Such formulations can also optionally contain one or more demulcents, preservatives, flavoring agents and/or coloring agents.

The pharmaceutical compositions can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

Other pharmaceutical compositions and methods of preparing pharmaceutical compositions are known in the art and are described, for example, in "*Remington: The Science* and Practice of Pharmacy" (formerly "Remingtons Pharmaceutical Sciences"); Gennaro, A., Lippincott, Williams & Wilkins, Philidelphia, Pa. (2000).

The pharmaceutical compositions of the present disclosure described above include one or more MPPs o in an amount effective to achieve the intended purpose. Thus the term "therapeutically effective dose" refers to the amount of the MPP that ameliorates the symptoms or characteristics of prostatitis. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other animals, including humans, using standard methods known in those of ordinary skill in the art.

Therapeutic efficacy and toxicity can also be determined by standard pharmaceutical procedures such as, for example, by determination of the median effective dose, or $ED_{50}$ (i.e. the dose therapeutically effective in 50% of the population) and the median lethal dose, or $LD_{50}$ (i.e. the dose lethal to 50% of the population). The dose ratio between therapeutic and toxic effects is known as the "therapeutic index," which can be expressed as the ratio, $LD_{50}/ED_{50}$. The data obtained from cell culture assays and animal studies can be used to formulate a range of dosage for human or animal use. The dosage contained in such compositions is usually within a range of concentrations that include the $ED_{50}$ and demonstrate little or no toxicity. The dosage varies within this range depending upon the dosage form employed, sensitivity of the subject, and the route of administration and the like.

The exact dosage to be administered to a subject can be determined by the practitioner, in light of factors related to the subject requiring treatment. Dosage and administration are adjusted to provide sufficient levels of the MPP and/or to maintain the desired effect. Factors which may be taken into account when determining an appropriate dosage include the severity of the disease state, general health of the subject, age, weight, and gender of the subject, diet, time and frequency of administration, drug combination(s), reaction sensitivities, and tolerance/response to therapy. Dosing regimens can be designed by the practitioner depending on the above factors as well as factors such as the half-life and clearance rate of the particular formulation.

Pharmaceutically effective amounts of MPPs can be formulated with pharmaceutically acceptable carriers for parenteral, oral, nasal, transrectal, transurethral, transperineal, intraprostatic, topical, transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. Slow or extended-release delivery systems, including any of a number of biopolymers (biological-based systems), systems employing liposomes, and polymeric delivery systems, can also be utilized with the compositions described herein to provide a continuous or long-term source of MPP. Such slow release systems are applicable to formulations, for example, for oral, topical and parenteral use.

The term "pharmaceutically acceptable carrier" refers to a carrier medium which does not interfere with the effectiveness of the biological activity of the active ingredients and which is not toxic to the host or patient. One skilled in the art may formulate the compounds of the present disclosure in an appropriate manner, and in accordance with accepted practices, such as those disclosed in Remington: The Science and Practice of Pharmacy, Gennaro, ed., Mack Publishing Co., Easton Pa., 19th ed., 1995.

In one embodiment, the MPP is conjugated to a water-soluble polymer, e.g., to increase stability or circulating half life or reduce immunogenicity. Clinically acceptable, water soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. Patent Pub. No. 20050106148 and references cited therein.

III. Use of MPPs for Treatment of Prostatitis

MPPs selectively target prostate cells relative to cells from other tissues. Thus, the MPPs are useful in the treatment or prevention of prostatitis.

In one embodiment, treatment of prostatitis refers to decrease in genitourinary and pelvic pain, voiding symptoms, and demonstrable prostatic inflammation. The size of the prostate gland can be measured in terms of its volume, by methods known in the art including, for example, planimetry, prolate ellipse volume calculation (HWL), and an ellipsoid volume measurement technique. Prostate size can also be measured directly, for example by digital rectal examination, or rectal ultrasound or cytoscopy, or indirectly, for example, by measuring changes in the levels of blood PSA or changes in the proportions of free and total PSA in the blood.

In one embodiment, administration of MPP decreases the volume of the prostate gland in a subject. For example, the disclosed methods can reduce prostate volume, for example, by at least 10%, at least 20%, or by at least 30% by at least 40%, or by at least 50%, such as about 5% to about 90%, including about 10% to about 70% percent, about 20% to about 50% (e.g., 10%, 20%, 30%, 40%, 50%, 60%, 70%, 80% or 90%) as compared to prostate volume prior to treatment or a standard reference known to be indicative of prostate volume in a subject afflicted with prostatitis.

In another embodiment, treatment of prostatitis refers to the decrease in the degree of severity of one or more symptoms of prostatitis. Symptoms of prostatitis include genitourinary and/or pelvic pain associated with changes or problems with urination, such as a hesitant, interrupted or weak stream, urgency and leaking or dribbling, or more frequent urination, especially at night resulting in significant impact on activities and general quality of life. These symptoms are also known as prostatitis-like symptoms. Prostatitis-like symptoms can be measured as known in the art using the National Institutes of Health-Chronic Prostatitis Symptom Index (NIH-CPSI) as well as the IPSS.

In another embodiment, treatment of prostatitis refers to the prevention or inhibition of histological inflammation of the prostate gland and can be measured by a reduction in the rate of increase in the inflammatory indices or reduction in symptoms of prostatitis as described above.

In some embodiments, following the administration of one or more therapies, subjects having prostatitis (for example, chronic prostatitis) are monitored to determine the response of their prostate to the therapy. For example, subjects are monitored to determine if the therapy resulted in a reduction in prostate gland size, alterations in leukocyte levels and/or reduction in one or more of the signs or symptoms associated with prostatitis, such as a reduction in genitourinary and/or pelvic pain associated with changes or problems with urination. In particular examples, subjects are analyzed one or more times, starting 7 days following treatment. Subjects can be monitored using any method known in the art including digital rectal examination, or rectal ultrasound or cytoscopy, or indirectly, for example, by measuring changes in the levels of blood PSA or changes in the proportions of free and total PSA in the blood.

In particular examples, if subjects are stable or have a minor, mixed or partial response to treatment, they can be re-treated after re-evaluation with the same schedule and preparation of compositions that they previously received for the desired amount of time, such as for at least three months, at least six months, at least twelve months, or at least twenty-four months of total treatment. For example, a partial response is one in which a reduction in size of the prostate gland is observed, but the subject still experiences pain with urination.

Selecting or Screening a Subject for Prostatitis

In some embodiments, subjects are pre-selected for therapy. For example, methods of treating prostatitis disclosed herein include selecting subjects in need of treatment for prostatitis, such as chronic prostatitis. In one example, subjects are identified as in need of the disclosed therapy by screening subjects to determine if they have one or more symptoms associated with prostatitis, including chronic prostatitis. For example, subjects are screened for chronic prostatitis by measuring leukocyte expression. Type IIIA (inflammatory) prostatitis is identified based on detection of an increase (such as at least a 10% increase) in leukocytes expressed in prostatic secretions or fluids, post prostatic massage urine, or semen as compared to known values of leukocytes in a subject not afflicted with prostatitis. Selecting subjects in need of treatment can also include identifying subjects experiencing one or more symptoms associated with prostatitis, including genitourinary and/or pelvic pain associated with changes or problems with urination, such as a hesitant, interrupted or weak stream, urgency and leaking or dribbling, or more frequent urination, sexual dysfunction, and/or psychologic alterations (particularly depression).

In some examples, subjects for treatment are selected by measuring the size of the prostate gland in terms of its volume, by methods known in the art including, for example, planimetry, prolate ellipse volume calculation (HWL), and an ellipsoid volume measurement technique. Prostate size can also be measured directly, for example by digital rectal examination, or rectal ultrasound or cytoscopy, or indirectly, for example, by measuring changes in the levels of blood PSA or changes in the proportions of free and total PSA in the blood. Subjects with at least a 20%, such as between 20% to 70% increase, 30% to 60% increase, 40% to 50% increase (e.g., 25%, 30%, 45%, 50%, 60%, 70%, 80%, 90%, 95% increase) in prostate volume as compared to a standardized volume (e.g., prostate volume in a subject that does not have prostatitis) indicates that the subject would benefit from the disclosed therapy. However, such pre-selecting is not required prior to administration of the therapeutic compositions disclosed herein.

Combination Therapy

The MPPs can be used alone or in combination with one or more additional treatments for prostatitis. The additional treatments for prostatitis include, but are not limited to, administration of drugs such as α-1-adrenoreceptor antagonists, neuromodulators, muscle relaxants, antibiotics, anti-inflammatory medications, 5-α reductase inhibitors, phytotherapies, surgical procedures, and minimally invasive techniques, etc., or any current therapy for prostatitis.

Examples of α-1-adrenoreceptor antagonists are alfuzosin/prazosin, tamsulosin, terazosin, and doxazosin. Examples of 5-α reductase inhibitors are finasteride and dutasteride. Examples of phytotherapies include Saw palmetto berry/dwarf palm (*Serenoa repens*), African plum bark (*Pygeum africanum*), South African star grass/beta-sitosterol (*Hipoxis rooperi*), Purple cone flower (*Echinacea purpurea*), Pumpkin seeds (*Cucurbita pepo*), Rye (*Secale cereale*), and Stinging nettle (*Urtica dioica*).

Examples of surgical procedures are transurethral resection of the prostate (TURP), transurethral needle ablation (TUNA), transurethral incision of the prostate (TUIP), transurethral microwave thermotherapy (TUMT), laser prostatectomy, balloon dilation, electrical vaporization and open prostatectomy.

If necessary to reduce a systemic immune response to the MPPs, immunosuppressive therapies can be administered in combination with the MPPs. Examples of immunosuppressive therapies include, but are not limited to, systemic or topical corticosteroids (Suga et al., *Ann. Thorac. Surg.* 73: 1092-1097, 2002), cyclosporin A (Fang et al., *Hum. Gene Ther.* 6: 1039-1044, 1995), cyclophosphamide (Smith et al., *Gene Ther.* 3: 496-502, 1996), deoxyspergualin (Kaplan et al., *Hum. Gene Ther.* 8:1095-1104, 1997) and antibodies to T and/or B cells (e.g., anti-CD40 ligand, anti CD4 antibodies, anti-CD20 antibody (Rituximab) (Manning et al., *Hum. Gene Ther.* 9: 477-485, 1998). Such agents can be administered before, during, or subsequent to administration of the MPP. The MPPs of the present disclosure may be administered separately, sequentially or simultaneously with the above noted treatments. In one example, antimicrobial agents that are routinely given to treat prostatitis are administered, such as fluoroquinolone or trimethoprim-sulfamethoxazole.

Administration of Therapeutically Effective Amount of MPPs

A therapeutically effective amount of an MPP, or a nucleic acid encoding an MPP, can be administered locally or systemically using methods known in the art, to subjects having prostatitis.

In one embodiment, the MPPs are injected into the prostate gland (intraprostatically) in a subject having prostatitis. For example, an administration approach similar to the multiple injection approach of brachytherapy can be used, in which multiple aliquots of the purified peptides, adapted as compositions or formulations and in the appropriate dosage form, may be injected using a needle through the perineum.

In addition, or alternatively, the MPPs can be administered systemically, for example intravenously, intramuscularly, subcutaneously, or orally, to a subject having prostatitis. A therapeutically effective amount of an MPP refers to an amount sufficient to achieve a desired biological effect, for example an amount that is effective to decrease the size (e.g., volume and/or weight) of the prostate gland, or attenuate further growth of the prostate gland, or decrease symptoms of prostatitis. In one embodiment, it is an amount sufficient to decrease the signs or symptoms of prostatitis in a subject. In particular examples, it is an amount effective to decrease the volume and/or weight of a prostate gland by at least 10%, 20%, 30%, 40%, or 50%. In another embodiment, it is an amount sufficient to prevent further increase in volume or weight of the prostate gland. Effective doses can be extrapolated from dose-response curves derived from in vitro or animal model test systems.

An effective amount of an MPP can be administered in a single dose, or in several doses, for example daily, during a course of treatment. However, the effective amount of MPP will be dependent on the subject being treated, the severity and type of the condition being treated, and the manner of administration. In one embodiment, a therapeutically effective amount of an MPP can vary from about 0.01 to 50 µg per gram prostate weight, administered intraprostatically. In another embodiment, a therapeutically effective amount of an MPP can vary from about 0.02 to 40 µg per gram prostate weight, administered intraprostatically. In another embodiment, a therapeutically effective amount of an MPP can vary from about 0.02 to 35 µg per gram prostate weight, administered intraprostatically. In another embodiment, a therapeutically effective amount of an MPP can vary from about 0.03 to 25 jag per gram prostate weight, administered intraprostatically. In another embodiment, a therapeutically effective amount of an MPP can vary from about 0.04 to 20 jag per gram prostate weight, administered intraprostatically. In another embodiment, a therapeutically effective amount of an MPP can vary from about 0.04 to 10 µg per gram prostate weight, administered intraprostatically.

In one embodiment, an effective intravenous dose of an MPP for a 70 kg human is from about 1 mg to about 10 mg of MPP. In another embodiment an effective intravenous dose is from about 1 mg to about 5 mg. In another embodiment, an effective intravenous dose is from about 1 mg to about 3 mg. In still another embodiment, an effective intravenous dose is about 2.8 mg. In one embodiment, an effective intraprostatic dose of an MPP for a 70 kg human is from about 10 mg to about 100 mg of MPP. In another embodiment, an effective intraprostatic dose of an MPP for a 70 kg human is from about 10 mg to about 50 mg of MPP. In another embodiment, an effective intraprostatic dose of an MPP for a 70 kg human is from about 10 mg to about 30 mg of MPP. In another embodiment, an effective intraprostatic dose of an MPP is about 28 mg for a 70 kg human.

In Vivo Expression of MPPs

As an alternative to (or in addition to) administration of MPPs to treat prostatitis, long term or systemic treatment of prostatitis, such as Type III prostatitis, can be achieved by expressing nucleic acids encoding MPPs in vivo.

Nucleic Acids Encoding MPPs

The present disclosure contemplates the use of nucleic acids or DNA molecules encoding MPPs for the treatment of prostatitis. Such DNA molecules can be obtained through standard molecular biology laboratory techniques and the sequence information disclosed herein.

Suitable DNA molecules and nucleotide include those which hybridize under stringent conditions to the DNA sequences disclosed (such as SEQ ID NO: 3), or fragments thereof, provided that they encode a functional MPP. Hybridization conditions resulting in particular degrees of stringency vary depending upon the nature of the hybridization method and the composition and length of the hybridizing DNA used. Generally, the temperature of hybridization and the ionic strength (especially the $Na^+$ concentration) of the hybridization buffer determines hybridization stringency. Calculations regarding hybridization conditions required for attaining particular amounts of stringency are discussed by Sambrook et al. (*Molecular Cloning: A Laboratory Manual*, Cold Spring Harbor, N.Y., 1989, Chapters 9 and 11). Hybridization with a target probe labeled with [$^{32}$P]-dCTP is generally carried out in a solution of high ionic strength such as 6.times.SSC at a temperature that is about 5-25° C. below the melting temperature, $T_m$. An example of stringent conditions is a salt concentration of at least about 0.01 to 1.0 M Na ion concentration (or other salts) at pH 7.0 to 8.3 and a temperature of at least about 30° C. for short probes (e.g., 10 to 50 nucleotides). Stringent conditions can also be achieved with the addition of destabilizing agents such as formamide. For example, conditions of 5.times.SSPE (750 mM NaCl, 50 mM Na phosphate, 5 mM EDTA, pH 7.4) at 25-30° C. are suitable for allele-specific probe hybridizations.

The degeneracy of the genetic code further allows for variations in the nucleotide sequence of a DNA molecule while maintaining the amino acid sequence of the encoded protein. For example, the amino acid Ala is encoded by the nucleotide codon triplet GCT, GCG, GCC and GCA. Thus, the nucleotide sequence could be changed without affecting the amino acid composition of the encoded protein or the characteristics of the protein. Based upon the degeneracy of the genetic code, variant DNA molecules may be derived from a reference DNA molecule using standard DNA mutagenesis techniques as described above, or by synthesis of DNA sequences. DNA sequences which do not hybridize under stringent conditions to the DNA sequences disclosed by virtue of sequence variation based on the degeneracy of the genetic code are also comprehended by this disclosure.

The present disclosure provides methods of expressing MPPs, for example a modified proaerolysin polypeptide in a cell or tissue in vivo. In one example, transfection of the cell or tissue occurs in vitro. In this example, the cell or tissue (such as a graft) is removed from a subject and then transfected with an expression vector containing a cDNA encoding the MMP protein of interest. The transfected cells will produce functional protein and can be reintroduced into the subject. In another example, a nucleic acid encoding the MMP protein of interest is administered to a subject directly (such as intravenous, or intraprostate), and transfection occurs in vivo.

The scientific and medical procedures required for human cell transfection are routine. A general strategy for transferring genes into donor cells is disclosed in U.S. Pat. No. 5,529,774. Generally, a gene encoding a protein having therapeutically desired effects is cloned into a viral expression vector, and that vector is then introduced into the target organism. The virus infects the cells, and produces the protein sequence in vivo, where it has its desired therapeutic effect (Zabner et al., *Cell* 75: 207-216, 1993).

It may only be necessary to introduce the DNA or protein elements into certain cells or tissues, for example, the prostate. However, in some instances, it may be more therapeutically effective and simple to treat all of a subject's cells, or more broadly disseminate the vector, for example by intravascular (i.v.) or oral administration.

The nucleic acid sequence encoding the MPP is under the control of a suitable promoter. Suitable promoters which can be used include, but are not limited to, the following promoters: a gene's native promoter, a retroviral LTR promoter; an adenoviral promoters, such as the adenoviral major late promoter; a CMV promoter; a RSV promoter; inducible promoters, such as the MMTV promoter; a metallothionein promoter; heat shock promoters; an albumin promoter; a histone promoter; TK promoters; B19 parvovirus promoters; and the ApoAI promoter. In one example, the promoter is a prostate-specific promoter, such as a probasin promoter. However the disclosure is not limited to specific foreign genes or promoters.

The recombinant nucleic acid can be administered to the subject by known methods, which allows the recombinant nucleic acid to reach the appropriate cells. These methods include injection, infusion, deposition, implantation, or topical administration. Injections can be intradermal or subcutaneous. The recombinant nucleic acid can be delivered as part of a viral vector, such as avipox viruses, recombinant vaccinia virus, replication-deficient adenovirus strains or poliovirus, or as a non-infectious form such as naked DNA or liposome encapsulated DNA, as further described below.

Adenoviral vectors include essentially the complete adenoviral genome (Shenk et al., *Curr. Top. Microbiol. Immunol.* 111: 1-39, 1984) and can be used to express an MMP-encoding nucleic acid. Alternatively, the adenoviral vector is a modified adenoviral vector in which at least a portion of the adenoviral genome has been deleted. In one example, the vector includes the following: an adenoviral 5' ITR; an adenoviral 3' ITR; an adenoviral encapsidation signal; a DNA sequence encoding a therapeutic agent; and a promoter for expressing the DNA sequence encoding a therapeutic agent. The vector is free of at least the majority of adenoviral E1 and E3 DNA sequences, but is not necessarily free of all of the E2 and E4 DNA sequences, and DNA sequences encoding adenoviral proteins transcribed by the adenoviral major late promoter. In another example, the vector is an adeno-associated virus (AAV) such as described in U.S. Pat. No. 4,797,368 (Carter et al.) and in McLaughlin et al. (*J. Virol.* 62: 1963-1973, 1988) and AAV type 4 (Chiorini et al., *J. Virol.* 71: 6823-6833, 1997) and AAV type 5 (Chiorini et al., *J. Virol.* 73: 1309-1319, 1999).

Such a vector can be constructed according to standard techniques, using a shuttle plasmid which contains, beginning at the 5' end, the following: an adenoviral 5' ITR; an adenoviral encapsidation signal; an E1 enhancer sequence; a promoter (which may be an adenoviral promoter or a foreign promoter); a tripartite leader sequence; a multiple cloning site (which may be as herein described); a poly A signal; and a DNA segment which corresponds to a segment of the adenoviral genome. The DNA segment serves as a substrate for homologous recombination with a modified or mutated adenovirus, and may encompass, for example, a segment of the adenovirus 5' genome no longer than from base 3329 to base 6246. The plasmid can also include a selectable marker and an origin of replication. The origin of replication may be a bacterial origin of replication. A desired DNA sequence encoding an MMP therapeutic agent can be inserted into the multiple cloning site of the plasmid. Examples of vectors which can be used to practice the methods disclosed herein include, but are not limited to, those disclosed in: WO 95/27512 to Woo et al.; WO 01/127303 to Walsh et al.; U.S. Pat. No. 6,221,349 to Couto et al.; U.S. Pat. No. 6,093,392 to High et al.

IV. Clinical Trials

To obtain regulatory approval for the use of MPPs to treat prostatitis clinical trials are performed. As is known in the art, clinical trials progress through phases of testing, which are identified as Phases I, II, III, and IV.

Initially the MPPs will be evaluated in a Phase I trial. Typically Phase I trials are used to determine the best mode of administration (for example, by pill or by injection), the frequency of administration, and the toxicity for the compounds. Phase I studies frequently include laboratory tests, such as blood tests and biopsies, to evaluate the effects of the potential therapeutic in the body of the patient. For a Phase I trial, a small group of patients with prostatitis are treated with a specific dose of MPP. During the trial, the dose is typically increased group by group in order to determine the maximum tolerated dose (MTD) and the dose-limiting toxicities (DLT) associated with the compound. This process determines an appropriate dose to use in a subsequent Phase II trial.

A Phase II trial can be conducted to further evaluate the effectiveness and safety of the MPP. In Phase II trials, the MPP is administered to groups of patients with prostatitis, using the dosage found to be effective in Phase I trials.

Phase III trials focus on determining how the MPP compares to the standard, or most widely accepted, treatment. In Phase III trials, patients are randomly assigned to one of two or more "arms". In a trial with two arms, for example, one arm will receive the standard treatment (control group) and the other arm will receive MPP treatment (investigational group).

Phase IV trials are used to further evaluate the long-term safety and effectiveness of an MPP. Phase IV trials are less common than Phase I, II and III trials and take place after the MPP has been approved for standard use.

Eligibility of Patients for Clinical Trials

Participant eligibility criteria can range from general (for example, age, sex, type of disease) to specific (for example, type and number of prior treatments, disease characteristics, blood cell counts, organ function). In one embodiment, eligible patients have been diagnosed with prostatitis. Eligibility criteria may also vary with trial phase. Patients eligible for clinical trials can also be chosen based on objective measurement of prostatitis, and failure to respond to other prostatitis treatments. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I trials usually include 15 to 30 participants for whom other treatment options have not been effective. Phase II trials typically include up to 100 participants who have already received drug therapy or surgery, but for whom the treatment has not been effective.

Participation in Phase II trials is often restricted based on the previous treatment received. Phase III trials usually include hundreds to thousands of participants. This large number of participants is necessary in order to determine whether there are true differences between the effectiveness of MPP and the standard treatment. Phase III can include patients ranging from those newly diagnosed with prostatitis to those with re-occurring prostatitis or prostatitis that did not respond to antibiotic treatment.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

Assessment of Patients Prior to Treatment

Prior to commencement of the study, several measures known in the art can be used to first classify the patients. Patients can first be assessed, for example by the NIH Chronic Prostatitis Symptom Index (NIH-CPSI) or the International Prostate Symptom Score (IPSS) system of seven questions. Patients can also be classified according to the type and/or stage of their disease and/or by prostate size.

Administration of MPP in Clinical Trials

MPP is typically administered to the trial participants by injection. In one embodiment, the MPP is administered by intraprostatic injection. A range of doses of the MPP can be tested. Provided with information from preclinical testing, a skilled practitioner could readily determine appropriate dosages of MPP for use in clinical trials. In one embodiment, a dose range is from about 0.01 µg/g prostate to about 50 µg/g prostate. In one embodiment, a dose range is from about 0.02 µg/g prostate to about 40 µg/g prostate. In one embodiment, a dose range is from about 0.02 µg/g prostate to about 35 µg/g prostate. In one embodiment, a dose range is from about 0.03 µg/g prostate to about 25 µg/g prostate. In one embodiment, a dose range is from about 0.04 µg/g prostate to about 20 µg/g prostate. In one embodiment, a dose range is from about 0.04 µg/g prostate to about 10 µg/g prostate. In one embodiment, a dose range is from about 0.1 µg/g prostate to about 5 µg/g prostate. In one embodiment, a dose range is from about 0.2 µg/g prostate to about 3 µg/g prostate. In one embodiment, a dose range is from about 0.5 µg/g prostate to about 2 µg/g prostate.

Pharmacokinetic Monitoring

To fulfill Phase I criteria, distribution of the MPP is monitored, for example, by chemical analysis of samples, such as blood or urine, collected at regular intervals. For example, samples can be taken at regular intervals up until about 72 hours after the start of infusion.

If analysis is not conducted immediately, the samples can be placed on dry ice after collection and subsequently transported to a freezer to be stored at −70° C. until analysis can be conducted. Samples can be prepared for analysis using standard techniques known in the art and the amount of MPP present can be determined, for example, by high-performance liquid chromatography (HPLC). Pharmacokinetic data can be generated and analyzed in collaboration with an expert clinical pharmacologist and used to determine, for example, clearance, half-life and maximum plasma concentration.

Monitoring of Patient Outcome

The endpoint of a clinical trial is a measurable outcome that indicates the effectiveness of a compound under evaluation. The endpoint is established prior to the commencement of the trial and will vary depending on the type and phase of the clinical trial. Examples of endpoints include, for example, decline in prostate volume, decline in blood PSA levels, improved urinary tract symptoms, improved urinary flow, and reduction in acute urinary retention. Other endpoints include toxicity and quality of life. For example, at least a 10% reduction in prostate volume or decline in PSA indicates the patient is responsive to the treatment.

V. Pharmaceutical Kits

The present disclosure additionally provides for therapeutic kits or packs containing one or more MPPs or a pharmaceutical composition including one or more MPPs for use in the treatment of prostatitis. The MPPs can be provided in the kit in unit dosage form. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kit can optionally further contain one or more other therapeutic agents for use in combination with the MPPs of the disclosure. The kit may optionally contain instructions or directions outlining the method of use or dosing regimen for the MPPs and/or additional therapeutic agents. When the components of the kit are provided in one or more liquid solutions, the liquid solution can be an aqueous solution, for example a sterile aqueous solution. In this case the container means may itself be an inhalant, syringe, pipette, eye dropper, or other such like apparatus, from which the composition may be administered to a patient or applied to and mixed with the other components of the kit.

The components of the kit may also be provided in dried or lyophilised form and the kit can additionally contain a suitable solvent for reconstitution of the lyophilised components (such as saline). Irrespective of the number or type of containers, the kits of the disclosure also include an instrument for assisting with the administration of the composition to a patient. Such an instrument may be an inhalant, syringe, pipette, forceps, measured spoon, eye dropper or similar medically approved delivery vehicle.

The disclosure is further illustrated by the following non-limiting Examples. Disclosure of certain specific examples is not meant to exclude other embodiments. In addition, any treatments described herein are not necessarily exclusive of other treatment, but can be combined with other bioactive agents or treatment modalities.

EXAMPLES

Example 1

Randomized, Double-Blinded Placebo-Controlled Clinical Trial for Transperineal Intraprostatic Injection of PRX302 to Treat Prostatitis This example describes a randomized, double-blinded, placebo-controlled study of transperineal intraprostatic injection of PRX302 under sonographic guidance for treatment of prostatitis.

Patients that exhibit one or more symptoms associated with prostatitis (such as prostate volume estimated at 30 to 100 mL as determined by TRUS; intolerant or refractory to α-blockers or 5-α reductase inhibitors; PSA values 4-10 ng/mL; and IPSS score of at least 15) are selected. Following completion of all screening procedures and confirmation of the subject's eligibility to enter the study, an electronic randomization process generates a randomization number for each subject. Subjects are randomly assigned to one of two treatment groups in a ratio of 2:1 between PRX302 and placebo groups, respectively stratified by prostate size and IPSS at baseline.

PRX302 is administered at a volume equivalent to 20% of the prostate volume and at a fixed concentration of 3 µg/mL. Placebo treatment includes normal 0.9% saline and is administered at a volume equivalent to 20% of prostate volume. Treatment is administered through a single injection under transrectal ultrasound (TRUS) guidance into the transition zone of the right and left lobes of the prostate. A minimum of two deposits is made along the needle track of each injection with a minimum of 1.0 mL delivered at each deposition point. For subjects receiving PRX302, the expected total dose range is between 18 to 60 µg.

Prophylactic antibiotic therapy (CIPRO® XL™ or equivalent) is administered from the day prior to dosing to the day following dosing to prevent urinary tract infection. Clinic visits/assessments are carried out at screening, Day 0, Day 3-5, Day 14, 1 month, 3 months, 6 months, 9 months and 12 months following treatment. Although the primary endpoint is analyzed when all 3-month data are available, the sponsor, investigators, and subjects will remain blinded to individual subject treatment assignments throughout the study. The parameters for efficacy evaluation are the following: (i) change from baseline in IPSS at 3 months; this is the primary endpoint; (ii) IPSS change from baseline at 1, 6, 9, and 12 months post treatment; (iii)proportion of IPSS responders at each follow-up time-point; (iv) change from baseline for IPSS obstructive and irritative subscores and the proportions of responders on each subscore at the follow-up time-points; and (v) QoL, Qmax, and prostate volume retention are expressed as change from baseline and assessed at 3, 6 and 12 months post treatment and prostate volume assessed at 3 and 6 months post treatment. Parameters for assessment of safety and tolerability of PRX302 will include adverse events, including serious adverse events (SAEs), physical examination, vital signs (heart rate, blood pressure, respiration rate, and temperature), ECG, clinical laboratory tests (hematology, serum chemistry, urinalysis, and PSA), and the International index for erectile function (IIEF) score. The International Prostate Symptom Score (IPSS) evaluates the frequency of the following symptoms representative of the last month's as reported by the subject's on a scale of 0 to 5 with 0 representing the most favorable response: (1) incomplete emptying; (2) frequency; (3) intermittency; (4) urgency; (5) weak stream; (6) straining; and (7) nocturia.

IPSS scores will be analyzed overall and for the irritative and obstructive domains. The irritative domain is calculated as the sum of the urgency, frequency and nocturia scores, and the obstructive domain is calculated as the sum of incomplete emptying, intermittency, weak stream and straining scores. For the IPSS total score and for each of the irritative and obstructive domains, subjects are classified as responders or non-responders at each time posttreatment point. For all 3 scores, a responder will be defined as a subject with a 30% decrease as compared with the baseline score.

The Quality of Life Questionnaire (QOL) includes a single question regarding the quality of life due to urinary symptoms, which states: "If you were to spend the rest of your life with your urinary condition the way it is now, how would you feel about that?" Response is provided on a scale of 0-6, with zero being the most favorable response (e.g., Delighted) and 6 is the least favorable (e.g., Terrible). A responder will be defined as a subject that rates their QOL as equal to or less than 3 (e.g., equally satisfied and dissatisfied).

Example 2

Treatment of Prostatitis in Human

This example describes a particular method that can be used to treat prostatitis in human afflicted with prostatitis.

A male experiencing one or more symptoms associated with prostatitis, including genitourinary and/or pelvic pain associated with changes or problems with urination (such as a hesitant, interrupted or weak stream, urgency and leaking or dribbling, or more frequent urination, sexual dysfunction, and/or psychologic alterations) or has least a 20% increase in prostate volume as compared to a standardized volume is selected for treatment of prostatitis.

PRX302 is administered at a volume equivalent to 20% of the prostate volume and at a fixed concentration of 3 μg/mL with the total dose being about 30 μg. Treatment is administered through a single injection under transrectal ultrasound (TRUS) guidance into the transition zone of the right and left lobes of the prostate.

Prostate size is measured after 7 days, 14 days and 30 days of initial treatment by digital rectal examination, or rectal ultrasound or cytoscopy, or indirectly, for example, by measuring changes in the levels of blood PSA or changes in the proportions of free and total PSA in the blood. Subjects with at least a 20% reduction in prostate volume and/or PSA levels as compared prior to treatment with PRX302 a standardized volume indicates that the prostatitis treatment is successful. Treatment can be re-administered as desired and in the presence of additional prostatitis agents.

What is claimed is:

1. A method of treating prostatitis in a subject having prostatitis, said method comprising intraprostatically administering to said subject a therapeutically effective amount of PRX302,
   wherein the PRX302 comprises an amino acid sequence having greater than 98% sequence identity to the amino acid sequence shown in SEQ ID NO:4 and which maintains the ability to selectively target and kill normal prostate cells, wherein the PRX302 comprises a polyhistidine tag;
   wherein said administering of the PRX302 results in a reduction in prostate volume.

2. The method of claim 1, wherein administration results in at least a 10% reduction in prostate volume.

3. The method of claim 1, wherein administration results in at least a 50% reduction in prostate volume.

4. The method of claim 1, wherein the prostatitis is chronic prostatitis.

5. The method of claim 1, further comprising administering an additional therapeutic agent for treating prostatitis.

6. The method of claim 5, wherein the additional therapeutic agent comprises an α-1-adrenoreceptor antagonist, an antibiotic, an anti-inflammatory agent, a 5α reductase inhibitor, a phytotherapy, or any combination thereof.

7. The method of claim 1, wherein the subject has one or more signs of prostatitis comprising a prostate volume of 30 to 100 mL, prostate specific antigen blood levels of 4-10 ng/mL, or a combination thereof.

8. The method of claim 1, wherein the polyhistidine tag comprises six histidine residues at the C-terminal end of PRX302 (SEQ ID NO:4).

9. A method of treating prostatitis in a subject having prostatitis, said method comprising intraprostatically administering to said subject a therapeutically effective amount of PRX302,
   wherein the PRX302 comprises an amino acid sequence having greater than 98% sequence identity to the amino acid sequence shown in SEQ ID NO:4 and which maintains the ability to selectively target and kill normal prostate cells, and a C-terminal polyhistidine tag that includes six histidine residues;
   wherein said administering of the PRX302 results in a reduction in prostate volume.

* * * * *